(12) United States Patent
Rosenblum et al.

(10) Patent No.: US 8,835,625 B2
(45) Date of Patent: *Sep. 16, 2014

(54) PROPARGYL SUBSTITUTED NUCLEOSIDE COMPOUNDS AND METHODS

(75) Inventors: Barnett Rosenblum, San Jose, CA (US); Geun-sook Jeon, Fullerton, CA (US); Shaheer Khan, Foster City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/470,181

(22) Filed: May 11, 2012

(65) Prior Publication Data

US 2012/0309953 A1 Dec. 6, 2012

Related U.S. Application Data

(63) Continuation of application No. 12/649,285, filed on May 11, 2012, now abandoned, which is a continuation of application No. 11/104,130, filed on Dec. 29, 2009, now abandoned, which is a continuation of application No. 11/015,319, filed on Dec. 17, 2004, now Pat. No. 7,998,706.

(60) Provisional application No. 60/532,614, filed on Dec. 23, 2003.

(51) Int. Cl.
| | |
|---|---|
| C07H 19/04 | (2006.01) |
| C07H 19/20 | (2006.01) |
| C07H 21/04 | (2006.01) |
| C07H 19/10 | (2006.01) |
| C07H 19/00 | (2006.01) |
| C07H 21/02 | (2006.01) |
| C07H 19/06 | (2006.01) |

(52) U.S. Cl.
CPC ............... *C07H 19/06* (2013.01); *C07H 21/04* (2013.01); *C07H 19/10* (2013.01); *C07H 19/00* (2013.01); *C07H 21/02* (2013.01)
USPC .................................................... 536/26.26

(58) Field of Classification Search
None
See application file for complete search history.

(56) References Cited

U.S. PATENT DOCUMENTS

| | | | | |
|---|---|---|---|---|
| 5,151,507 | A | 9/1992 | Hobbs et al. | |
| 6,232,103 | B1 | 5/2001 | Short | |
| 6,248,568 | B1 * | 6/2001 | Khan et al. | 435/91.1 |
| 6,335,440 | B1 * | 1/2002 | Lee et al. | 536/26.6 |
| 6,504,024 | B2 * | 1/2003 | Khan et al. | 536/26.26 |
| 6,811,979 | B2 * | 11/2004 | Taing et al. | 435/6.12 |
| 7,399,854 | B2 * | 7/2008 | Lee et al. | 536/26.6 |
| 7,998,706 | B2 * | 8/2011 | Rosenblum et al. | 435/91.1 |
| 2010/0113759 | A1 | 5/2010 | Rosenblum et al. | |

FOREIGN PATENT DOCUMENTS

CA 2411514 9/2000

OTHER PUBLICATIONS

White et al., "Total Synthesis of Epothilone B, Epothilone D, and cis— and trans-9-,10-Dehydroepothilone D," Journal of the Amer. Chem. Society, 123(23), 5407-5413 (2001): Web published May. 16, 2001; cited in the disclosure at p. 31, lines 20-21.*
Stephens et al., "The Substitution of Aryl Iodides with Cuprous Acetylides. A Synthesis of Tolanes and Heterocycles," Journal of Organic Chemistry, 28(12), 3313-3315 (Dec. 1963); cited in the disclosure at p. 31, line 21.*
White et al., "Total Synthesis of Epothilone B, Epothilone D, and cis- and trans-9-,10-Dehydroepothilone D," Journal of the Amer. Chem. Society, 123(23), 5407-5413 (2001): Web published May. 16, 2001; cited in the disclosure at p. 31, lines 20-21.*
Tabor et al., "DNA Sequence Analysis with a Modified Bacteriophage T7 DNA Polymerase," The Journal of Biological Chemistry, 265(14), 8322-8328 (May. 15, 1990).*
International Search Report from PCT/US2004/042383 mailed on Jun. 27, 2005.
Darby, R.A.J., "Base Analogues and Ligands for Stabilising Triple Helical Nucleid Acids", *Dissertation Abstract International , Ann Arbor, MI, U.S.A., 64:1,* 2003, 92-c.
Dupret, D , "New Technique for Fine Structure DNA Analysis using hybridization with a set of modified oligonucleotides ", *Biomedical and Health Research, 23,* 1998, pp. 244-255.
Lazrek, Hassan B. et al., "Synthesis of Novel Branched Nucleoside Dimers Containing a 1, 2, 3,-Triazolyl Linkage", *Nucleosides and Nucleotides, 17:9-11,* 1998, pp. 1851-1856.
Stephens, et al., "The Substitution of Aryl Iodides with Cuprous Acetylides. A Synthesis of Tolanes and Heterocycles", *Journal of Organic Chemistry,* Dec. 1963, pp. 3313-3315.
White, et al., "Total Synthesis of Epothilone B, Epothilone D, and cis- and trans-9-, 10- Dehydroepothilone D", *Journal of the Amer. Chem. Society,* May. 16, 2001, pp. 5407-5413.
Yan, Yuan et al., "Identification of Nucleotides with Identical Fluorescent Labels Based on Fluorescence Polarization in Surfactant Solutions", *Analytical Chemistry, 73:18,* 2001, pp. 4508-4513.

* cited by examiner

*Primary Examiner* — Lawrence E Crane

(57) ABSTRACT

Disclosed, among other things, are compounds having the structure

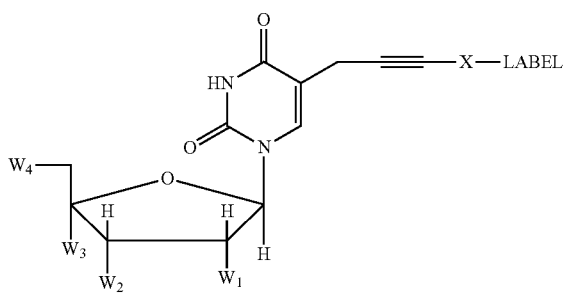

wherein X comprises a bond or a linker, LABEL comprises at least one detectable label, $W_1$ taken alone is —H or —OH, $W_2$ is —OH or a non-extendable moiety, $W_3$ when taken alone is —H or when taken together with $W_1$ is —$CH_2$—O—, and $W_4$ is OH, monophosphate, diphosphate, or triphosphate. Also disclosed are labeled polynucleotide compounds and methods of use thereof.

43 Claims, No Drawings

PROPARGYL SUBSTITUTED NUCLEOSIDE COMPOUNDS AND METHODS

This application is a Continuation of U.S. patent application Ser. No. 12/649,285, filed Dec. 29, 2009, now abandoned, which is a Continuation of U.S. patent application Ser. No. 11/104,130, filed Apr. 12, 2005, which is a Continuation of U.S. patent application Ser. No. 11/015,319, filed Dec. 17, 2004, now U.S. Pat. No. 7,998,706, which claims a priority benefit under 35 U.S.C. §119(e) from U.S. Patent Application No. 60/532,614, filed Dec. 23, 2003, each of which is incorporated herein by reference in its entirety.

The present teachings relate to nucleobase, nucleoside and nucleotide compounds, methods of synthesis, and uses thereof, The present teachings provide compounds, such as nucleobase, nucleoside and/or nucleotide compounds including a propargyl linker, and methods for making or using such compounds.

Unless stated otherwise, the following terms and phrases as used herein are intended to have the following meanings:

The term "detectable label" refers to any moiety that, when attached to the compounds of the present teachings, render such nucleosides, and polynucleotides containing such nucleotides, detectable using known detection means. Exemplary detectable labels include but are not limited to fluorophores, chromophores, radioisotopes, spin-labels, enzyme labels, chemiluminescent labels that allow for direct detection of a labeled compound by a suitable detector, or a binding pair, for example, a ligand, such as an antigen or biotin, that can bind specifically with high affinity to a detectable anti-ligand, such as a labeled antibody or avidin. In some embodiments the labels can be fluorescent dyes such as fluorescein or rhodamine dyes.

The term "pyrimidine nucleobase" refers to a compound comprising a pyrimidine ring. It will be understood that a pyrimidine nucleobase can be any naturally occurring pyrimidine nucleobase known in the art, including but not limited to, uracil, thymine and cytosine. The term "pyrimidine nucleobase analog" refers to heterocyclic compounds comprising at least one ring nitrogen atom capable of forming a covalent bond to a sugar or sugar analog. Examples of pyrimidine nucleobase analogs (in the form of nucleobases, nucleosides or nucleotides), include but are not limited to the following exemplary structures, for which preparatory methods or commercial sources can be found by suitable structure searching in available databases such as Chem Abstracts Service (CAS), SciFinder, and the like.

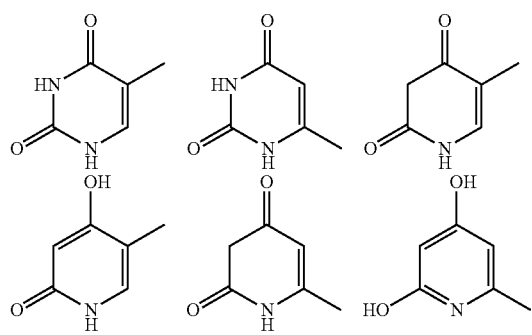

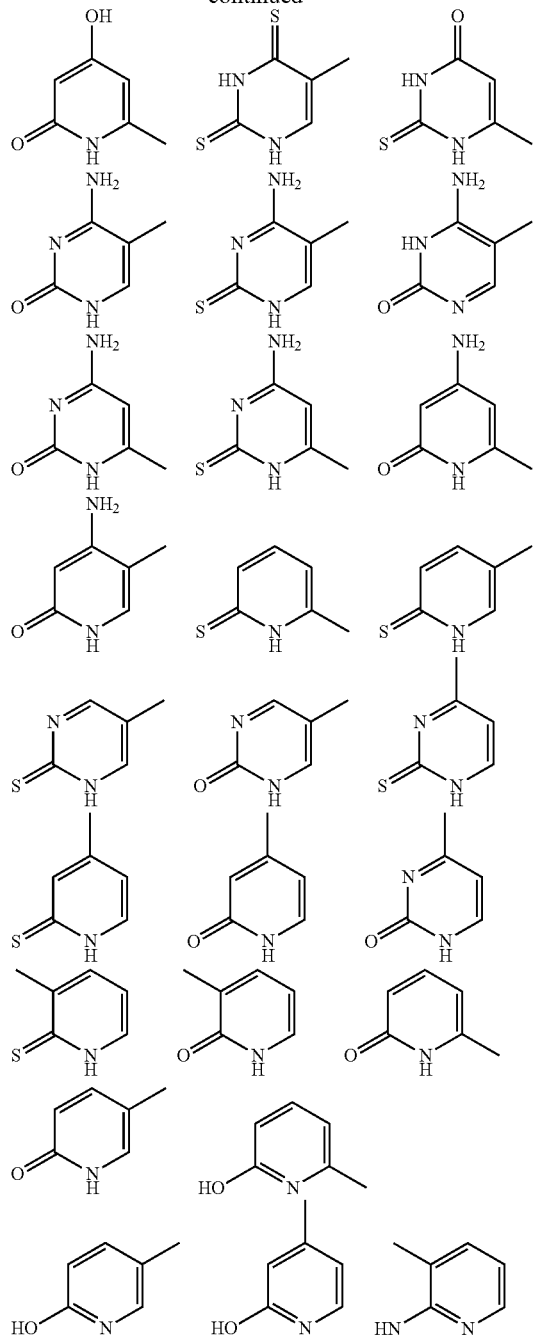

The term "nucleoside" and "nucleotide" refers to a compound having a pyrimidine nucleobase, for example cytosine, uracil or thymine linked to a pentose at the 1' position, including 2'-deoxy and 2'-hydroxyl forms. The term "nucleotide" as used herein refers to a phosphate ester of a nucleoside, e.g., triphosphate esters, wherein the most common site of esterification is the hydroxyl group attached at the C-5 position of the pentose. "Nucleoside analog" and "nucleotide analog" refers to compounds having modified nucleobase moieties (e.g., pyrimidine nucleobase analogs described above), modified sugar moieties, and/or modified phosphate ester moieties (e.g., see Scheit, Nucleoside Analogs, John Wiley and Sons, 1980; F. Eckstein, Ed., Oligonucleotides and Analogs, Chapters 8 and 9, IRL Press, 1991). Examples of nucleoside analogs and nucleotide analogs include but are not limited to those that comprise a pyrimidine nucleobase analog.

As used herein "thymidine" and "thymidylate" refer to the 2'-deoxy forms of the thymine nucleoside and nucleotide respectively.

As used herein, the term "polynucleotide" refers to polymers of natural nucleotide monomers or analogs thereof, including double and single stranded deoxyribonucleotides, ribonucleotides, α-anomeric forms thereof, and the like. Usually the nucleoside monomers are linked by phosphodiester linkages, where as used herein, the term "phosphodiester linkage" refers to phosphodiester bonds or bonds including phosphate analogs thereof, and include associated counterions, including but not limited to $H^+$, $NH_4^+$, $Na^+$, if such counterions are present. Polynucleotides typically range in size from a few monomeric units, e.g. 8-40, to several thousands of monomeric units. Whenever a polynucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. "Polynucleotide analog" includes, for example, polynucleotides in which at least one nucleoside monomer unit is a nucleoside analog and/or at least one phosphate ester internucleoside linkage is a phosphate ester analog, as defined above under "nucleotide analog". Exemplary classes of polynucleotide analogs are those in which the sugar and internucleoside linkages are replaced with an uncharged, neutral amide, such as a morpholino-carbamate and peptide nucleic acids ("PNA"). Further exemplary PNAs are those having a N-(2-aminoethyl)-glycine amide backbone (see, e.g., Nielsen et al., 1991, Science 254:1497-1500). PNA sequences represented as a sequence of letters are preceded with the letter "p" and expressed parenthetically, e.g., "p(ATGCCTG)." In such representations, it is understood that the amino terminus is at the left-hand side (equivalent to the 5' end in polynucleotides) and the carboxyl terminus is at the right-hand side (equivalent to the 3' end in polynucleotides).

The term "phosphate analog" refers to analogs of phosphate wherein the phosphorous atom is in the +5 oxidation state and one or more of the oxygen atoms is replaced with a non-oxygen moiety, exemplary analogs include, but are not limited to phosphorothioate, phosphorodithioate, phosphoroselenoate, phosphorodiselenoate, phosphoroanilothioate, phosphoranilidate, phosphoramidate, boronophosphates, and associated counterions, including but not limited to $H^+$, $NH_4^+$, $Na^+$, if such counterions are present.

As used herein, the term "sugar analog" refers to analogs of the sugar ribose. Exemplary ribose sugar analogs include, but are not limited to, substituted or unsubstituted furanoses having more or fewer than 5 ring atoms, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, —OR, —NRR or halogen groups, where each R is independently —H, ($C_1$-$C_6$) alkyl or ($C_1$-$C_{14}$) aryl. Examples of substituted furanoses having 5 ring atoms include but are not limited to 2'-deoxyribose, 2'-($C_1$-$C_6$)alkylribose, 2'-($C_1$-$C_6$)alkoxyribose, 2'-($C_5$-$C_{14}$)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-amino-ribose, 2'-deoxy-3'-($C_1$-$C_6$)alkylribose, 2'-deoxy-3'-($C_1$-$C_6$)alkoxyribose, 2'-deoxy-3'-($C_5$-$C_{14}$)aryloxyribose, 3'-($C_1$-$C_6$)alkylribose-5'-triphosphate, 2'-deoxy-3'-($C_1$-$C_6$)alkylribose-5'-triphosphate, 2'-deoxy-3'-($C_1$-$C_6$)alkoxyribose-5'-triphosphate, 2'-deoxy-3'-($C_5$-$C_{14}$)aryloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate. Further sugar analogs include but are not limited to, for example

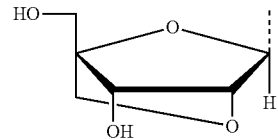

and those described in Wengel, et al. WO 99/14226, incorporated herein by reference.

As used herein the term "primer-extension reagent" means a reagent including components necessary to affect the enzymatic template-mediated extension of an polynucleotide primer. Primer extension reagents include: (i) a polymerase enzyme, e.g., a thermostable polymerase enzyme such as Taq polymerase; (ii) a buffer; (iii) chain-extension nucleotides, e.g., a deoxynucleotide triphosphate, e.g., deoxyguanosine 5'-triphosphate, 7-deazadeoxyguanosine 5'-triphosphate, deoxyadenosine 5'-triphosphate, deoxythymidine 5'-triphosphate, deoxycytidine 5'-triphosphate; and, optionally in the case of Sanger-type DNA sequencing reactions, (iv) one or more chain-terminating nucleotides, e.g., dideoxynucleotide triphosphates, e.g., dideoxyguanosine 5'-triphosphate, 7-deazadideoxyguanosine 5'-triphosphate, dideoxyadenosine 5'-triphosphate, dideoxythymidine 5'-triphosphate, and dideoxycytidine 5'-triphosphate.

"Template nucleic acid" refers to any nucleic acid that can be presented in a single stranded form and is capable of annealing with a primer polynucleotide. Exemplary template nucleic acids include DNA, RNA, which DNA or RNA may be single stranded or double stranded. More particularly, template nucleic acid may be genomic DNA, messenger RNA, cDNA, DNA amplification products from a PCR reaction, and the like. Methods for preparation of template DNA may be found elsewhere (ABI PRISM™ Dye Primer Cycle Sequencing Core Kit).

In some embodiments, nucleoside and/or nucleotide compounds herein may be used as substrates for polymerase enzymes, may be incorporated into polynucleotides, and may be employed in various methods such as primer extension reactions (e.g., in Sanger-type DNA sequencing methods and polymerase chain reactions).

Some embodiments of the present teachings provide for labeled nucleosides and/or nucleotides comprising a nucleobase disposed between a sugar or a sugar analog and a propargylic moiety, where the nucleobase comprises a pyrimidine nucleobase or a pyrimidine nucleobase analog, the propargylic moiety can be covalently attached to the nucleobase at one of the C-3, C-4, C-5 or C-6 position of the nucleobase, the sugar or sugar analog can be covalently attached to the nucleobase at the N-1 position of the nucleobase, the sugar or sugar analog can be substituted by a monophosphate group, a diphosphate group or a triphosphate group, and the propargylic moiety comprises a propargyl group covalently attached to the nucleobase at the methylene carbon of the propargyl group, a detectable label, and a linker covalently linking the acetylene carbon of the propargyl group to the detectable label.

Alternatively, in some embodiments the present teachings provide for compounds that can optionally be described by the general structures (I)

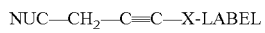
(I)

where NUC can be a nucleobase selected from a pyrimidine nucleobase or a pyrimidine nucleobase analog, a nucleoside comprising a pyrimidine nucleobase or a pyrimidine nucleobase analog or a nucleotide comprising a pyrimidine nucleobase or a pyrimidine nucleobase analog, X can be a bond or a linker, and LABEL can be a detectable label. In some embodiments, the propargyl group (—$CH_2$—C≡C—) can be attached by its $CH_2$ group to NUC at, for example, one of the C-3, C-4, C-5 or C-6 of NUC. In some embodiments, the propargyl group can be attached by its $CH_2$ group to NUC at, for example, one of C-5 or C-6 of NUC, or when NUC is a 3-deazapyrimidine, can be attached by its $CH_2$ group to NUC at the 3-position, or when NUC is a 4-deaminated pyrimidine, can be attached by its $CH_2$ group to NUC at the 4-position. In each of the preceding examples the numbering of the pyrimidine or pyrimidine analog is such that the position attached to the sugar moiety is given the position number 1 as is customary in the art. In some embodiments, X comprises a terminal $CH_2$ group that is linked to the acetylene carbon of the propargyl group.

Alternatively, some embodiments of the present teachings provide for compounds that can optionally be described by the general structure (II)

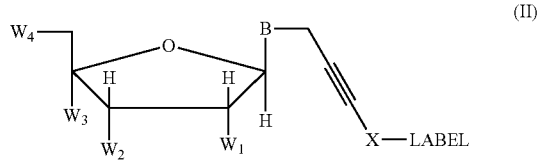

where B comprises a pyrimidine or a pyrimidine analog, X can be a bond or a linker, LABEL comprises a detectable label, $W_1$ taken alone is —H and —OH, $W_2$ is —OH or a non-extendable moiety, $W_3$ taken alone is —H or when taken together with $W_1$ is —$CH_2$—O—, and $W_4$ is monophosphate, diphosphate, triphosphate, or —OH. When $W_1$ is —OH the nucleoside is a ribonucleoside, and when $W_1$ is —H the nucleoside is a deoxyribonucleoside. In some embodiments, the propargyl group (—$CH_2$—C≡C—) can be attached to B at, for example, C-3, C-4, C-5 or C-6. In some embodiments, the propargyl group can be attached to B at, for example, C-5 or C-6 of B, or when B is a 3-deazapyrimidine the propargyl group can be attached to B at the 3-position, or when B is a 4-deaminated pyrimidine, the propargyl group can be attached to B at the 4-position.

In some embodiments $W_2$ can be one of —H, azido, amino, halo (e.g., fluoro or chloro), methoxy. In some embodiments, $W_2$ is —H or fluoro.

Optionally, in some embodiments useful for enzymatic synthesis of polynucleotides, $W_4$ is —$P_3O_{10}$.

When $W_1$ is —OH the compound can be a ribonucleoside or a ribonucleotide, and when $W_1$ is —H the compound can be a deoxyribonucleoside or a dideoxyribonucleotide.

In some embodiments, the present teachings provide compounds that can optionally be described by the general structure (III)

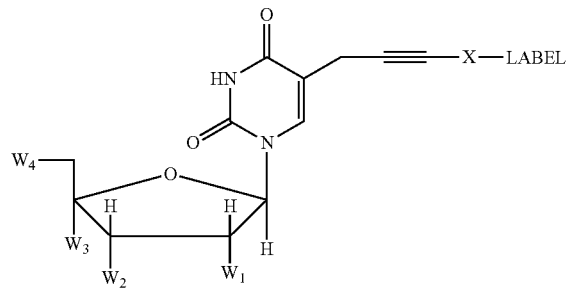
III where X, $W_1$, $W_2$, $W_3$, and $W_4$ are as described above.

In some embodiments $W_2$ can be one of —H, azido, amino, halo (e.g., fluoro or chloro), methoxy. In some embodiments, $W_2$ is —H or fluoro.

Optionally, in some embodiments useful for enzymatic synthesis of polynucleotides, $W_4$ is —$P_3O_{10}$.

The compounds of the present teachings can optionally include a linker X that can take on a wide variety of forms. For example, the linker may comprise from 1-50 linker chain atoms selected from C, N, O, S, P and Si. However, the linker need not be limited to groups containing C, N, O, S, P and Si. Furthermore, the linker can optionally be a bond, such that the label is covalently attached to the acetylene carbon of the propargyl group. In some embodiments the linker can be made up of one or more linker elements that can be the same or different. For example, the linker can comprise a single linker element repeated one or more times or the linker can comprise a plurality of distinct linker elements repeated alone or in combination one or more times.

In some embodiments the linker can comprise a diradical selected from

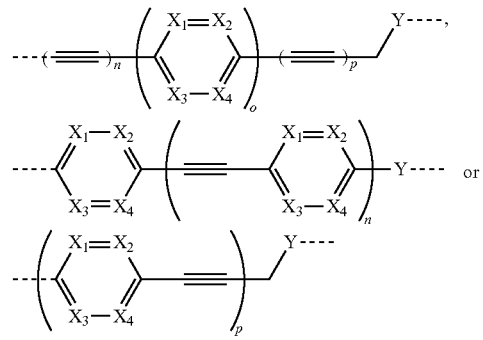

where n can be an integer from 0 to 9, o can be an integer from 1 to 10, p can be an integer from 1 to 10, $X_1$, $X_2$, $X_3$ and $X_4$ can each independently be selected from carbon or nitrogen, $X_1$, $X_2$, $X_3$ and $X_4$ can be substituted or unsubstituted, Y can optionally be selected from oxygen, sulfur, unsubstituted amine, substituted amine, phosphonate and phosphate, where Y can be covalently attached to at least one further linker element or to at least one detectable label, and the opposite end of the diradical can be covalently attached to at least one further linker element or to the propargyl group. In some embodiments $X_1$, $X_2$, $X_3$ and $X_4$ can be carbon. In some embodiments $X_1$, $X_2$, $X_3$ and $X_4$ can be unsubstituted. It will be understood by one of skill in the art that the integer n can be any integer from 0 to 9, for example, n can be any one of 0, 1, 2, 3, 4, 5, 6, 7, 8 and 9, the integer o can be any integer from 1 to 10, for example, o can be anyone of 1, 2, 3, 4, 5, 6, 7, 8, 9 and 10, and the integer p can be any integer from 1 to 10, for example, p can be any one of 1, 2, 3, 4, 5, 6, 7, 8, 9 and 10. In some embodiments the above linkers are incorporated into compounds of the present teachings such that an aryl or alkynyl end of the diradical is positioned closer to the propargyl group and the Y terminus is positioned closer to the detectable label.

In some embodiments the linker can comprise a diradical selected from

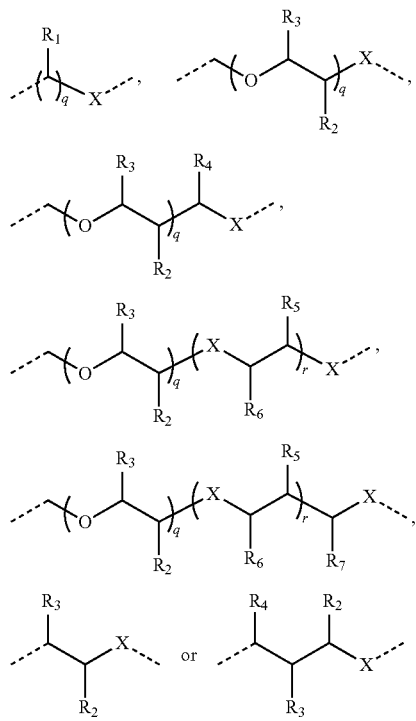

where each X can be independently selected from oxygen, sulfur, —NR— and —NH—, where R, $R_1$, $R_2$, $R_3$, $R_4$, $R_5$, $R_6$, and $R_7$, taken alone, can each be independently selected from H, and C1-C4 alkyl (such as methyl); $R_2$ taken together with one of $R_3$ or $R_4$ can form a substituted or unsubstituted carbocyclic ring having from 5-7 carbon atoms, $R_3$ taken together with one of $R_2$ or $R_4$ can form a substituted or unsubstituted carbocyclic ring having from 5-7 carbon atoms, $R_5$ taken together with $R_6$ can form a substituted or unsubstituted carbocyclic ring having from 5-7 carbon atoms, q can be an integer from 1-10 and r can be an integer from 1-10, X can be covalently attached to at least one further linker element or to at least one detectable label, and the opposite end of the diradical can be covalently attached to at least one further linker element or to the propargyl group. It will be understood by one of skill in the art that the integer q can be any integer from 1 to 10, for example, q can be any one of 1, 2, 3, 4, 5, 6, 7, 8, 9 and 10, and the integer can be any integer from 1 to 10, for example, r can be any one of 1, 2, 3, 4, 5, 6, 7, 8, 9 and 10. In some embodiments the above linkers are incorporated into the compounds of the present teachings such that the aryl or alkynyl end of the diradical is positioned closer to the propargyl group and the X terminus is positioned closer to the detectable label.

In some embodiments the linker can optionally include at least one diradical selected from

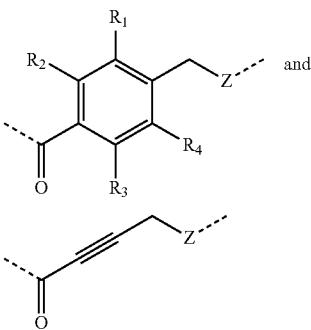

where $R_1$, $R_2$, $R_3$ and $R_4$. are each independently selected from H, halogen, F, Cl, Br, I, alkyl, and $C_1$-$C_{10}$ aryl, Z is selected from oxygen, sulfur, substituted amine and unsubstituted amine, and the carbonyl carbon is covalently attached to X, Y or is the end of the diradical closer to the propargyl group. In some embodiments $R_1$, $R_2$, $R_3$ and $R_4$ are H. In some embodiments Z is an unsubstituted amine. In some embodiments Z is a substituted amine. In some embodiments Z can be covalently attached to at least one further linker element or to at least one detectable label, and the opposite end of the diradical can be covalently attached to at least one further linker element or to the propargyl group.

In some embodiments, the linker may comprise one or more of the following diradicals

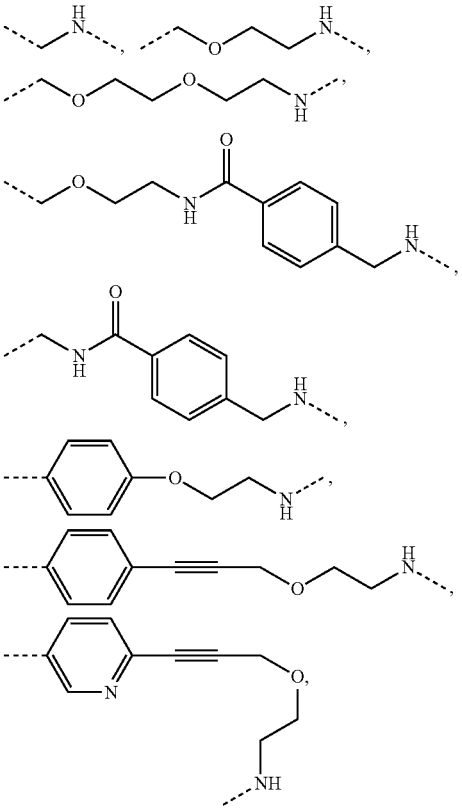

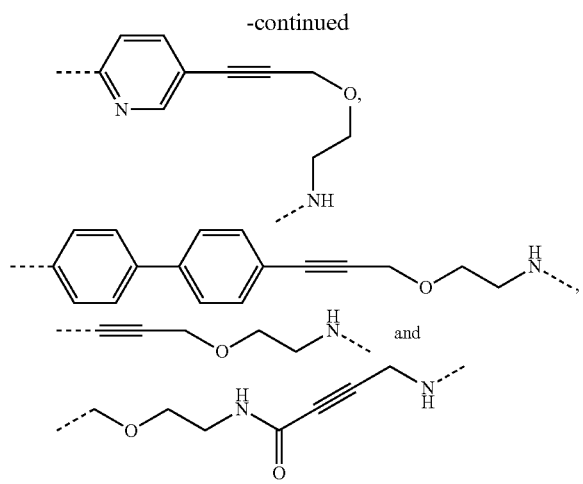

where the amine terminus is optionally covalently attached to a label and the opposite terminus is covalently attached to the acetylene carbon atom of the propargyl group.

In some embodiments the label can optionally be attached to the linker through a linkage formed by the reaction of a nucleophilic moiety of the linker with a complementary functionality located on the label. The complementary functionality can be, for example, isothiocyanate, isocyanate, acyl azide, N-hydroxysuccinimide (NHS) ester, sulfonyl chloride, aldehyde or glyoxal, epoxide, carbonate, aryl halide, imidoester, carbodiimide, anhydride, 4,6-dichlorotriazinylamine, or other active carboxylate, see Hermanson, *Bioconjugate Techniques*, Academic Press, 1996. For example, in some embodiments the complementary functionality can optionally be an activated NHS ester that reacts with a nucleophilic moiety on the linker. The activated NHS ester on the label can be formed by reacting a label, including a carboxylate complementary functionality, with dicyclohexylcarbodiimide and N-hydroxysuccinimide to form the NHS ester. By way of example, Table 1 shows a sampling of representative complementary functionalities and resulting linkages formed by reaction of the complementary functionality with an amine moiety on the linker.

TABLE 1

| Complementary Functionality | Linkage |
|---|---|
| —NCS | —NCSNH— |
| 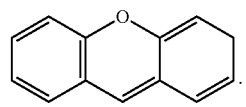 | 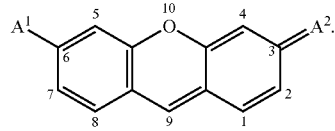 |
| —SO₂X | —SO₂NH— |
| $\begin{array}{c}\text{O}\\\parallel\\—\text{C}—\text{O}—\text{N}\end{array}$ (NHS ester) | $—\overset{\text{O}}{\underset{\parallel}{\text{C}}}—\overset{\text{H}}{\underset{\mid}{\text{N}}}—$ |

When the compounds of the present teachings include a detectable label, the label can be any moiety that, when attached to the compounds of the present teachings, renders the compound to which the label is attached detectable using known detection means. Examples of such labels include but are not limited to fluorophores, chromophores, radioisotopes, spinlabels, enzyme labels, and chemiluminescent labels. Furthermore, the label can optionally be, for example, a ligand, such as an antigen, or biotin, which can bind specifically with high affinity to a detectable anti-ligand, such as a labeled antibody or avidin.

In some embodiments, detectable labels comprise fluorescent dyes such as fluorescein, rhodamine, rhodol or energy transfer dyes. For example, various fluorescent dyes are described in U.S. Patent Application Publication US 2002/0102590 A1, which is incorporated herein by reference In some embodiments, the dye comprises a xanthene-type dye, which contains a fused three-ring system of the form:

This parent xanthene ring may be unsubstituted (i.e., all substituents are H) or may be substituted with one or more of a variety of the same or different substituents, such as described below.

In some embodiments, the dye contains a parent xanthene ring having the general structure:

In the parent xanthene ring depicted above, $A^1$ is OH or $NH_2$ and $A^2$ is O or $NH_2^+$. When $A^1$ is OH and $A^2$ is O, the parent xanthene ring is a fluorescein-type xanthene ring. When $A^1$ is $NH_2$ and $A^2$ is $NH_2$ the parent xanthene ring is a rhodamine-type xanthene ring. When $A^1$ is $NH_2$ and $A^2$ is O, the parent xanthene ring is a rhodol-type xanthene ring. In the parent xanthene ring depicted above, one or both nitrogens of $A^1$ and $A^2$ (when present) and/or one or more of the carbon atoms at positions C-1, C-2, C-4, C-5, C-7, C-8 and C-9 can be independently substituted with a wide variety of the same or different substituents. In some embodiments, typical substituents include, but are not limited to, —X, —R, —OR, —SR, —NRR, perhalo $(C_1$-$C_6)$—$CF_3$, —CN, —OCN, —SCN, —NCO, —NCS, —NO, —NO₂, —N₃, —S(O)₂O⁻, —S(O)₂OH, —S(O)₂R, —C(O)R, —C(O)X, —C(S)R, —C(S)X, —C(O)OR, —C(O)O⁻, —C(S)OR, —C(O)SR, —C(S)SR, —C(O)NRR, —C(S)NRR and —C(NR)NRR, where each X is independently a halogen (preferably —F or CO and each R is independently hydrogen, $(C_1$-$C_6)$ alkyl, $(C_1$-$C_6)$ alkanyl, $(C_1$-$C_6)$ alkenyl, $(C_1$-$C_6)$ alkynyl, $(C_5$-$C_{20})$ aryl, $(C_6$-$C_{26})$ arylalkyl, $(C_5$-$C_{20})$ arylaryl, heteroaryl, 6-26 membered heteroarylalkyl 5-20 membered heteroaryl-heteroaryl, carboxyl, acetyl, sulfonyl, sulfinyl, sulfone, phosphate, or phosphonate. Moreover, the C-1 and C-2 substituents and/or the C-7 and C-8 substituents can be taken together to form substituted or unsubstituted buta[1,3]dieno or $(C_5$-$C_{20})$ aryleno bridges. Generally, substituents which do not tend to quench the fluorescence of the parent xanthene ring are preferred, but in some embodiments quenching substituents may be desirable. Substituents that tend to quench fluorescence of parent xanthene rings are electron-withdrawing groups, such as —$NO_2$, —Br, and —I. In some embodiments, C-9 is unsubstituted. In another embodiment, C-9 is substituted with a phenyl group. In another embodiment, C-9 is substituted with a substituent other than phenyl.

When $A^1$ is $NH_2$ and/or $A^2$ is $NH_2^+$, these nitrogens can be included in one or more bridges involving the same nitrogen atom or adjacent carbon atoms, e.g., ($C_1$-$C_{12}$) alkyldiyl, ($C_1$-$C_{12}$) alkyleno, 2-12 membered heteroalkyldiyl and/or 2-12 membered heteroalkyleno bridges.

Any of the substituents on carbons C-1, C-2, C-4, C-5, C-7, C-8, C-9 and/or nitrogen atoms at C-3 and/or C-6 (when present) can be further substituted with one or more of the same or different substituents, which are typically selected from —X, —R', =O, —OR', SR', =S, —NR'R', =NR', —$CX_3$, —CN, —OCN, —SCN, —NCO, —NCS, —NO, —$NO_2$, =$N_2$, —$N_3$, —NHOH, —$S(O)_2O^-$, —$S(O)_2OH$, —$S(O)_2R'$, —$P(O)(O^-)_2$, —$P(O)(OH)_2$, —C(O)R', —C(O)X, —C(S)R', —C(S)X, —C(O)OR', —$C(O)O^-$, —C(S)OR', —C(O)SR', —C(S)SR', —C(O)NR'R', —C(S)NR'R' and —C(NR)NR'R', where each X is independently a halogen (preferably —F or —Cl) and each R' is independently hydrogen, ($C_1$-$C_6$) alkyl, 2-6 membered heteroalkyl, ($C_5$-$C_{14}$) aryl or heteroaryl, carboxyl, acetyl, sulfonyl, sulfinyl, sulfone, phosphate, or phosphonate.

Exemplary parent xanthene rings include, but are not limited to, rhodamine-type parent xanthene rings and fluorescein-type parent xanthene rings.

In some embodiments, the dye contains a rhodamine-type xanthene dye that includes the following ring system:

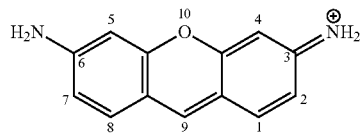

In the rhodamine-type xanthene ring depicted above, one or both nitrogens and/or one or more of the carbons at positions C-1, C-2, C-4, C-5, C-7 or C-8 can be independently substituted with a wide variety of the same or different substituents, as described above for the parent xanthene rings, for example. Exemplary rhodamine-type xanthene dyes include, 15 but are not limited to, the xanthene rings of the rhodamine dyes described in U.S. Pat. Nos. 5,936,087, 5,750,409, 5,366,860, 5,231,191, 5,840,999, 5,847,162, and 6,080,852 (Lee et al.), PCT Publications WO 97/36960 and WO 99/27020, Sauer et al., *J. Fluorescence* 5(3):247-261 (1995), Arden-Jacob, *Neue Lanwellige Xanthen-Farbstoffe für Fluoreszenzsonden and Farbstoff Laser*, Verlag Shaker, Germany (1993), and Lee et al., *Nucl. Acids Res.* 20:2471-2483 (1992). Also included within the definition of "rhodaminetype xanthene ring" are the extended-conjugation xanthene rings of the extended rhodamine dyes described in U.S. application Ser. No. 09/325,243 filed Jun. 3, 1999, published as U.S. Patent Publication 2009/0305433A1, now U.S. Pat. No. 7,797,042.

In another embodiment, the dye comprises a fluorescein-type parent xanthene ring having the structure:

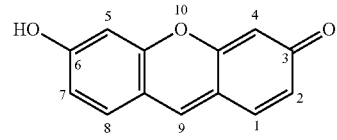

In the fluorescein-type parent xanthene ring depicted above, one or more of the carbons at positions C-1, C-2, C-4, C-5, C-7, C-8 and C-9 can be independently substituted with a wide variety of the same or different substituents, as described above for the parent xanthene rings. Exemplary fluorescein-type parent xanthene rings include, but are not limited to, the xanthene rings of the fluorescein dyes described in U.S. Pat. Nos. 4,439,356, 4,481,136, 5,188,934, 5,654,442, and 5,840,999, WO 99/16832, and EP 050684. Also included within the definition of "fluorescein-type parent xanthene ring" are the extended xanthene rings of the fluorescein dyes described in U.S. Pat. Nos. 5,750,409 and 5,066,580.

In another embodiment, the dye comprises a rhodamine dye, which comprises a rhodamine-type xanthene ring in which the C-9 carbon atom is substituted with an orthocarboxy phenyl substituent (pendent phenyl group). Such compounds are also referred to herein as orthocarboxyfluoresceins. A particularly preferred subset of rhodamine dyes are 4,7,-dichlororhodamines. Typical rhodamine dyes include, but are not limited to, rhodamine B, 5-carboxyrhodamine, rhodamine X (ROX), 4,7-dichlororhodamine X (dROX), rhodamine 6G (R6G), 4,7-dichlororhodamine 6G, rhodamine 110 (R110), 4,7-dichlororhodamine 110 (dR110), tetramethyl rhodamine (TAMRA) and 4,7-dichloro-tetramethyl-rhodamine (dTAMRA). Additional rhodamine dyes can be found, for example, in U.S. Pat. No. 5,366,860 (Bergot et al.), U.S. Pat. No. 5,847,162 (Lee et al.), U.S. Pat. No. 6,017,712 (Lee et al.), U.S. Pat. No. 6,025,505 (Lee et al.), U.S. Pat. No. 6,080,852 (Lee et al.), U.S. Pat. No. 5,936,087 (Benson et al.), U.S. Pat. No. 6,111,116 (Benson et al.), U.S. Pat. No. 6,051,719 (Benson et al.), U.S. Pat. Nos. 5,750,409, 5,366,860, 5,231,191, 5,840,999, and 5,847,162, U.S. application Ser. No. 09/325,243 filed Jun. 3, 1999, published as U.S. Patent Publication 2009/0305433A1, now U.S. Pat. No. 7,797,042, PCT Publications WO 97/36960 and WO 99/27020, Sauer et al., 1995, J. Fluorescence 5(3):247-261, Arden-Jacob, 1993, *Neue Lanwellige Xanlhen-Farbstoffe für Fluoresenzsonden and Farbstoff Laser*, Verlag Shaker, Germany, and Lee et al., *Nucl. Acids Res.* 20(10):2471-2483 (1992), Lee et al., *Nucl. Acids Res.* 25:2816-2822 (1997), and Rosenblum et al., *Nucl. Acids Res.* 25:4500-4504 (1997), for example. In some embodiments, the dye is a 4,7-dichloro-orthocarboxyrhodamine.

In some embodiments, the dye comprises a fluorescein dye, which comprises a fluorescein-type xanthene ring in which the C-9 carbon atom is substituted with an orthocarboxy phenyl substituent (pendent phenyl group). A preferred subset of fluorescein-type dyes are 4,7,-dichlorofluoresceins. Typical fluorescein dyes include, but not limited to, 5-carboxyfluorescein (5-FAM), 6-carboxyfluorescein (6-FAM). Additional typical fluorescein dyes can be found, for example, in U.S. Pat. Nos. 5,750,409, 5,066,580, 4,439,356, 4,481,136, 5,188,934 (Menchen et al.), 5,654,442 (Menchen et al.), 6,008,379 (Benson et al.), and 5,840,999, PCT publication WO 99/16832, and EPO Publication 050684. In some embodiments, the dye is a 4,7-dichloro-orthocarboxyfluorescein.

In some embodiments, the dye can be a cyanine, phthalocyanine, squaraine, or bodipy dye, such as described in the following references and references cited therein: U.S. Pat. No. 5,863,727 (Lee et al.), U.S. Pat. No. 5,800,996 (Lee et al.), U.S. Pat. No. 5,945,526 (Lee et al.), U.S. Pat. No. 6,080,868 (Lee et al.), U.S. Pat. No. 5,436,134 (Haugland et al.), U.S. Pat. No. 5,863,753 (Haugland et al.), U.S. Pat. No. 6,005,113 (Wu et al.), and WO 96/04405 (Glazer et al.).

Rhodamine dyes for use in connection with the present teachings can include, for example, a rhodamine dye having the structure:

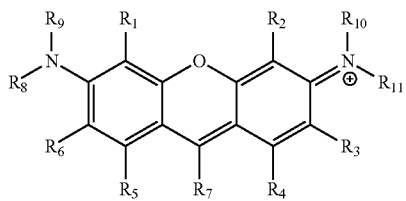

where $R_1$-$R_6$ are each independently selected from —H, —F, —Cl, —Br, —I, —CN, —$CO_2H$, —$CO_2X$, —$CO_2R$, —$SO_3H$, —$SO_3X$, —$SO_3R$, halogen, $C_1$-$C_{10}$ alkyl, $C_1$-$C_{10}$ alkenyl, $C_1$-$C_{10}$ alkynyl, $C_1$-$C_{10}$ alkoxy, $C_1$-$C_{10}$ alkylamine, $C_1$-$C_{10}$ mercaptyl, alkylsulfonate, $C_3$-$C_{10}$ cycloalkyl, $C_4$-$C_{10}$ cycloalkenyl, $C_3$-$C_{10}$ heterocyclic, $C_3$-$C_{10}$ aromatic, $C_5$-$C_6$ heteroaromatic, where each alkyl, alkenyl, alkynyl, alkoxy, alkylamine, mercaptyl, alkylsulfonate, cycloalkyl, cycloalkenyl, heterocyclic, aromatic and heteroaromatic is optionally further substituted by F, Cl, Br, I, —$CO_2H$, —$CO_2X$, —$CO_2R$, —$SO_3H$, —$SO_3X$ or —$SO_3R$ where X is a counterion and R is $C_1$-$C_6$ alkyl, $R_8$-$R_{11}$ are each independently selected from $C_1$-$C_{10}$ alkyl, $C_1$-$C_{10}$ alkenyl, $C_1$-$C_{10}$ alkynyl, $C_1$-$C_{10}$ alkoxy, $C_1$-$C_{10}$ alkylamine, $C_1$-$C_{10}$ mercaptyl, $C_1$-$C_{10}$ alkylsulfonate, $C_3$-$C_{10}$ cycloalkyl, $C_4$-$C_{10}$ cycloalkenyl, $C_3$-$C_{10}$ aromatic, benzyl, benzoyl, biphenyl where each alkyl, alkenyl, alkynyl, alkoxy, alkylamine, mercaptyl, alkylsulfonate, cycloalkyl, cycloalkenyl, aromatic, benzyl, benzoyl and biphenyl is optionally further substituted by F, Cl, Br, I, —$CO_2H$, —$CO_2X$, —$CO_2R$, —$SO_3H$, —$SO_3X$ or —$SO_3R$ where X is a counterion and R is $C_1$-$C_6$ alkyl, $R_1$ taken together with $R_9$ forms a 5-7 membered ring that is saturated or unsaturated, and is optionally substituted by one or more $C_1$-$C_6$ alkyl, $C_1$-$C_6$ alkylamine or $C_1$-$C_6$ alkylsulfonate moieties, $R_2$ taken together with $R_{10}$ forms a 5-7 membered ring that is saturated or unsaturated, and is optionally substituted by one or more $C_1$-$C_6$ alkyl, $C_1$-$C_6$ alkylamine or $C_1$-$C_6$ alkylsulfonate moieties, $R_3$ taken together with $R_4$ forms a benzo or naphtha ring optionally substituted by one or more of —F, —Cl, —Br, —I, —CN, —$CO_2H$, —$CO_2X$, —$CO_2R$, —$SO_3H$, —$SO_3X$, —$SO_3R$, halogen, $C_1$-$C_{10}$ alkyl, $C_1$-$C_{10}$ alkenyl, $C_1$-$C_{10}$ alkynyl, $C_1$-$C_{10}$ alkoxy, $C_1$-$C_{10}$ alkylamine, mercaptyl, alkylsulfonate, $C_3$-$C_{10}$ cycloalkyl, $C_4$-$C_{10}$ cycloalkenyl, $C_3$-$C_{10}$ heterocyclic, $C_3$-$C_{10}$ aromatic, $C_5$-$C_6$ heteroaromatic, where each alkyl, alkenyl, alkynyl, alkoxy, alkylamine, mercaptyl, alkylsulfonate, cycloalkyl, cycloalkenyl, heterocyclic, aromatic and heteroaromatic is optionally further substituted by F, Cl, Br, I, —O—, —S—, —NH—, —NR— —$CO_2H$,
—$CO_2X$, —$CO_2R$, —$SO_3H$, —$SO_3X$ or —$SO_3R$ where X is a counterion and R is $C_1$-$C_6$ alkyl, $R_5$ taken together with $R_6$ forms a benzo or naphtha ring optionally substituted by one or more of —F, —Cl, —Br, —I, —CN, —$CO_2H$, —$CO_2X$, —$CO_2R$, —$SO_3H$, —$SO_3X$, —$SO_3R$, halogen, $C_1$-$C_{10}$ alkyl, $C_1$, —$C_{10}$ alkenyl, $C_1$-$C_{10}$ alkynyl, $C_1$-$C_{10}$ alkoxy, $C_1$-$C_{10}$ alkylamine, $C_1$, —$C_{10}$ mercaptyl, $C_1$-$C_{10}$ alkylsulfonate, $C_3$-$C_{10}$ cycloalkyl, $C_4$-$C_{10}$ cycloalkenyl, $C_3$-$C_{10}$ heterocyclic, $C_3$-$C_{10}$ aromatic, $C_5$-$C_6$ heteroaromatic, where each alkyl, alkenyl, alkynyl, alkoxy, alkylamine, mercaptyl, alkylsulfonate, cycloalkyl, cycloalkenyl, heterocyclic, aromatic and heteroaromatic is optionally further substituted by F, Cl, Br, I, —$CO_2H$, —$CO_2X$, $CO_2R$, —$SO_3H$, —$SO_3X$ or —$SO_3R$ where X is a counterion and R is $C_1$, —$C_6$ alkyl, $R_3$ taken together with $R_{11}$ forms a 5- or 6-membered ring that is saturated or unsaturated, and is optionally substituted by one or more $C_1$-$C_6$ alkyl, $C_1$-$C_6$ alkylamine or $C_1$-$C_6$ alkylsulfonate moieties, $R_6$ taken together with $R_8$ forms a 5- or 6-membered ring that is saturated or unsaturated,' and is optionally substituted by one or more $C_1$-$C_6$ alkyl, $C_1$-$C_6$ alkylamine or $C_1$-$C_6$ alkylsulfonate moieties, $R_7$ is selected from —H, —F, —CN, —$CO_2H$, —$CO_2X$, —$CO_2R$, $C_1$-$C_{10}$ alkyl, $C_1$-$C_{10}$ alkyl that is saturated or unsaturated and is optionally substituted by one or more —F, —Cl, —Br, $CO_2H$, —$CO_2X$, —$CO_2R$, —$SO_3H$, —$SO_3X$, —$SO_3R$, where X is a counterion and R is $C_1$-$C_6$ alkyl, or $R_7$ is a radical of the formula:

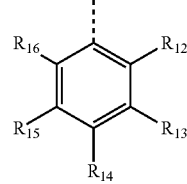

wherein $R_{12}$, $R_{13}$, $R_{14}$, $R_{15}$ and $R_{16}$ are each independently selected from —H, —F, —Cl, —Br, —I, —$CO_2H$, —$CO_2X$, —$CO_2R$, —$SO_3H$, $SO_3X$, and —$SO_3R$, where X is a counterion and R is $C_1$-$C_6$ alkyl.

Exemplary rhodamine dyes useful labels in connection with the present teachings include, but are not limited to, tetramethylrhodamine (TAMRA), 4,7-dichlorotetramethyl rhodamine (DTAMRA), rhodamine X (ROX), 4,7-dichlororhodamine X (DROX), rhodamine 6G (R6G), rhodamine 110 (R110), 4,7-dichlororhodamine 110 (R110) and the like. Further examples of possible rhodamine dyes that can be used in connection with the present teachings include those described in Menchen, et. al. U.S. Pat. No. 6,583,168, Bergot, et. al. U.S. Pat. No. 5,366,860, Lee, et. al. U.S. Pat. No. 6,191,278, Lam, et. al. U.S. Pat. No. 6,248,884, Herrmann, et. al. U.S. Pat. No. 5,750,409, Mao, et. al., U.S. Pat. No. 6,130,101 add 1830 PCT, Lee, et. al. Nucleic Acids Research, 20(10), 2471-2483 (1992) each of which is incorporated herein by reference.

In some cases the designation −1 or −2 is placed after an abbreviation of a particular dye, e.g., TAMRA-1. The "−1" and "−2" designations indicate the particular 5 or 6 dye isomer being used. The 1 and 2 isomers are defined by the elution order (the 1 isomer being the first to elute) of free dye in a reverse-phase chromatographic separation system utilizing a C-8 column and an elution gradient of 15% acetonitrile/85% 0.1 M triethylammonium acetate to 35% acetonitrile/65% 0.1 M triethylammonium acetate.

Fluorescein dyes for use in connection with the present teachings can include, for example, any fluorescein dye having the structure:

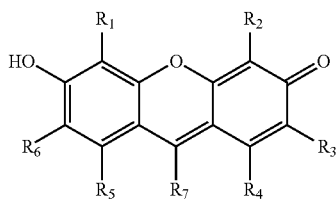

where $R_1$-$R_6$ are each independently selected from —H, —F, —Cl, —Br, —I, —CN, —$CO_2H$, —$CO_2X$, $CO_2R$, —$SO_3H$, —$SO_3X$, —$SO_3R$, halogen, $C_1$-$C_{10}$ alkyl, $C_1$-$C_{10}$ alkenyl, $C_1$-$C_{10}$ alkynyl, $C_1$-$C_{10}$ alkoxy, $C_1$-$C_{10}$ alkylamine, $C_1$-$C_{10}$ mercaptyl, $C_1$-$C_{10}$ alkylsulfonate, $C_3$-$C_{10}$ cycloalkyl, $C_4$-$C_{10}$ cycloalkenyl, $C_3$-$C_{10}$ heterocyclic, $C_3$-$C_{10}$ aromatic, $C_5$-$C_6$ heteroaromatic, where each alkyl, alkenyl, alkynyl, alkoxy, alkylamine, mercaptyl, alkylsulfonate, cycloalkyl, cycloalkenyl, heterocyclic, aromatic and heteroaromatic is optionally further substituted by F, Cl, Br, I, —$CO_2H$, —$CO_2X$, —$CO_2R$, —$SO_3H$, —$SO_3X$ or —$SO_3R$ where X is a counterion and R is $C_1$-$C_6$ alkyl, $R_3$ taken together with $R_4$ forms a benzo or naphtha ring optionally substituted by —F, —Cl, —Br, —I, —CN, —$CO_2H$, —$CO_2X$, —$CO_2R$, —$SO_3H$, —$SO_3X$, —$SO_3R$, halogen, $C_1$-$C_{10}$ alkyl, $C_1$-$C_{10}$ alkenyl, $C_1$-$C_{10}$ alkynyl, $C_1$-$C_{10}$ alkoxy, $C_1$-$C_{10}$ alkylamine, $C_1$-$C_{10}$ mercaptyl, $C_1$-$C_{10}$ alkylsulfonate, $C_3$-$C_{10}$ cycloalkyl, $C_4$-$C_{10}$ cycloalkenyl, $C_3$-$C_{10}$ heterocyclic, $C_3$-$C_{10}$ aromatic, $C_5$-$C_6$ heteroaromatic, where each alkyl, alkenyl, alkynyl, alkoxy, alkylamine, mercaptyl, alkylsulfonate, cycloalkyl, cycloalkenyl, heterocyclic, aromatic and heteroaromatic is optionally further substituted by F, Cl, Br, I, —$CO_2H$, —$CO_2X$, —$CO_2R$, —$SO_3H$, —$SO_3X$ or —$SO_3R$ where X is a counterion and R is $C_1$-$C_6$ alkyl, $R_5$ taken together with $R_6$ forms a benzo or naphtha ring optionally substituted by —F, —Cl, —Br, —I, —CN, —$CO_2H$, —$CO_2X$, —$CO_2R$, —$SO_3H$, —$SO_3X$, —$SO_3R$, halogen, $C_1$-$C_{10}$ alkyl, $C_1$-$C_{10}$ alkenyl, $C_1$-$C_{10}$ alkynyl, $C_1$-$C_{10}$ alkoxy, $C_1$-$C_{10}$ alkylamine, $C_1$-$C_{10}$ mercaptyl, $C_1$-$C_{10}$ alkylsulfonate, $C_3$-$C_{10}$ cycloalkyl, $C_4$-$C_{10}$ cycloalkenyl, $C_3$-$C_{10}$ heterocyclic, $C_3$-$C_{10}$ aromatic, $C_5$-$C_6$ heteroaromatic, where each alkyl, alkenyl, alkynyl, alkoxy, alkylamine, mercaptyl, alkylsulfonate, cycloalkyl, cycloalkenyl, heterocyclic, aromatic and heteroaromatic is optionally further substituted by F, Cl, Br, I, —$CO_2H$, —$CO_2X$, —$CO_2R$, —$SO_3H$, —$SO_3X$ or —$SO_3R$ where X is a counterion and R is $C_1$-$C_6$ alkyl, $R_7$ is selected from —H, —F, —CN, —$CO_2H$, —$CO_2X$, —$CO_2R$, $C_1$-$C_{10}$ alkyl, $C_1$-$C_{10}$ alkyl that is saturated or unsaturated and is optionally substituted by one or more —F, —Cl, —Br, —$CO_2H$, —$CO_2X$, —$CO_2R$, —$SO_3H$, —$SO_3X$, —$SO_3R$, where X is a counterion and R is $C_1$-$C_6$ alkyl, or $R_7$ is a radical of the formula:

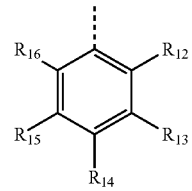

wherein $R_{12}$, $R_{13}$, $R_{14}$, $R_{15}$ and $R_{16}$ are each independently selected from —H, —F, —Cl, —Br, —I, —$CO_2H$, —$CO_2X$, —$CO_2R$, —$SO_3H$, —$SO_3X$, and $SO_3R$, where X is a counterion and R is $C_1$-$C_6$ alkyl.

Exemplary rhodamine dyes useful labels in connection with the present teachings include, but are not limited to, 6-carboxyfluorescein, 5-carboxyfluorescein, 5-carboxy-4,7, 2',7'-tetrachlorofluorescein, 6-carboxy-4,7,2',7'-tetrachlorofluorescein, 5-carboxy-4,7,2',4',5',7'-hexachlorofluorescein, 6-carboxy-4,7,2',4',5',7'-hexachlorofluorescein, 5-carboxy-4',5'-dichloro-2' 7'-dimethoxy-fluorescein, 6-carboxy-4',5'-dichloro-2'7'-dimethoxyfluorescein and 5-carboxy-2',4',5',7'-tetrachlorofluorescein.

In some embodiments of the present teachings, nucleoside and/or nucleotide compounds comprise a nucleobase disposed between a sugar or a sugar analog and a propargylic moiety that, among other uses, are useful in the preparation of the compounds of the present teachings. In some embodiments, the nucleobase can be selected from a pyrimidine nucleobase or a pyrimidine nucleobase analog, the propargylic moiety can be covalently attached to the nucleobase at one of the C-3, C-4, C-5 or C-6 position of the nucleobase, the sugar or sugar analog can be covalently attached to the nucleobase at the N-1 position of the nucleobase, and wherein the propargylic moiety can include a propargyl group covalently attached to the nucleobase at the methylene carbon of the propargyl group. In some embodiments at least one linker can be covalently attached to the acetylene carbon of the propargyl group.

Alternatively, some embodiments of the present teachings provide for compounds that can optionally be described by the general structure (IV)

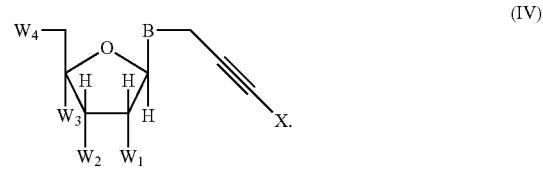

(IV)

where B can be a nucleobase selected from a pyrrnidine or a pyrimidine analog, X can be a hydrogen or a linker, $W_1$ taken alone is —H and —OH, $W_2$ is —OH or a non-extendable moiety, $W_3$ taken alone is —H or when taken together with $W_1$ is —$CH_2$—O—, and $W_4$ is monophosphate, diphosphate, triphosphate, or —OH. When $W_1$ is —OH the nucleoside is a ribonucleoside, and when $W_1$ is —H the nucleoside is a deoxyribonucleoside. In some embodiments, the propargyl group (—$CH_2$—C≡C—) can be attached to B at, for example, C-3, C-4, C-5 or C-6. In some embodiments, the propargyl group can be attached to B at, for example, C-5 or C-6 of B, or when B is a 3-deazapyrimidine the propargyl group can be attached to B at the 3-position, or when B is a 4-deaminated pyrimidine, the propargyl group can be attached to B at the 4-position.

In some embodiments $W_2$ can be one of —H, azido, amino, halo (e.g., fluoro or chloro), methoxy. In some embodiments, $W_2$ is —H or fluoro.

Optionally, in some embodiments useful for enzymatic synthesis of polynucleotides, $W_4$ is —$P_3O_{10}$.

When $W_1$ is —OH the compound can be a ribonucleoside or a ribonucleotide, and when $W_1$ is —H the compound can be a deoxyribonucleoside or a dideoxyribonucleotide.

Alternatively, in some embodiments, the present teachings provide for compounds that can optionally be described by the general structure (V)

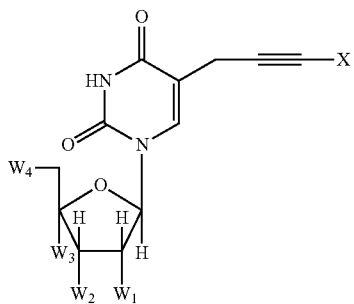

V where X can be hydrogen or a linker, and $W_1$, $W_2$, $W_3$ and $W_4$ are as described above.

In some embodiments $W_2$ can be one of —H, azido, amino, halo (e.g., fluoro or chloro), methoxy. In some embodiments, $W_2$ is —H or fluoro.

Optionally, in some embodiments useful for enzymatic synthesis of polynucleotides, $W_4$ is —$P_3O_{10}$.

In some embodiments, the present teachings provide labeled polynucleotide comprising at least one labeled nucleotide having a nucleobase disposed between a sugar or a sugar analog and a propargylic moiety, where the nucleobase can be selected from a pyrimidine nucleobase or a pyrimidine nucleobase analog, the propargylic moiety can be covalently attached to the nucleobase at one of the C-3, C-4, C-5 or C-6 position of the nucleobase, the sugar or sugar analog can be covalently attached to the nucleobase at the N-1 position of the nucleobase, and the propargylic moiety can comprise a propargyl group covalently attached to the nucleobase at the methylene carbon of the propargyl group. In some embodiments a linker can be covalently attached to the acetylene carbon of the propargyl group. In some embodiments a label can be covalently attached to the linker.

In some embodiments, the present teachings provide polynucleotides comprising at least one labeled nucleotide in accordance with any of structures (I), (II), and (III) above.

In some embodiments, the polynucleotide terminates at its 3' end with a labeled nucleotide in accordance with any of structures (I), (II), and (III) above that is not extendable by a DNA polymerase. In some embodiments, $W_2$ is not OH. In some embodiments, $W_2$ is H, azido, amino, halo, or methoxy. In some embodiments, $W_2$ is —H or fluoro.

The present compounds can be prepared by any of a number of possible methods. Without being limiting in any way, three possible alternative strategies for the synthesis of the compounds of the present teachings are described herein.

In one approach, referred to herein as the "convergent synthesis method," sub-elements of a an alkynyl group, a linker, S, and an optional label (collectively referred to herein as a "propargylic moiety" when the optional label is included and collectively referred to herein as a "propargylic moiety" when the optional label is not included) are assembled prior to their attachment to a nucleoside. Then one of the fully assembled linker label conjugate or propargylic moiety is attached to a nucleobase, nucleoside or nucleotide (collectively referred to herein as "nucleobase compound") in a single reaction step.

Another approach, referred to herein as a "linear synthesis method," a first element of the propargylic moiety is covalently attached to a nucleobase compound to form a nucleobase compound conjugate optionally followed by subsequent optional activation of the first element of the propargylic moiety to affect the attachment of a second element of the propargylic moiety. The optional addition of further elements is then repeated until all of the elements of the propargylic moiety are incorporated onto the nucleobase compound conjugate. Alternatively, the propargylic moiety of the nucleobase compound conjugate can then optionally be activated and contacted with a reagent capable of covalently attaching at least one label to form a compound of the present teachings. It will be recognized by one skilled in the art that activation of the nucleobase compound conjugate for further coupling reactions is optional. In other words, subsequent coupling steps can be carried out with no activation of the nucleobase compound conjugate. In some embodiments, the element or elements to be covalently attached can optionally be activated contacted with an unactivated nucleobase compound conjugate.

Another approach combines the strategies of both convergent and linear synthesis. That is, some elements of the propargylic moiety or the propargylic moiety are pre-assembled into a multi-element intermediate, and this intermediate is then attached to an element that has already been incorporated onto the nucleobase compound. It will be readily understood by one of skill in the art that the preferred strategy for the preparation of a given compound of the present teaching will depend on the convenience of the individual coupling chemistries, and their compatibility with the functional groups on the desired compound.

In some embodiments, methods of making the compounds of the present teachings can comprise contacting a 5-halomethyl (e.g., 5-bromomethyl or 5-iodomethyl)pyrimidine nucleobase or a 5-halomethylpyrimidine nucleobase analog with an acetylide anion to form an adduct comprising a propargyl substituted pyrimidine or a propargyl substituted pyrimidine analog.

In some embodiments the acetylide anion can comprise at least one label covalently attached thereto in which case the coupling of the acetylide anion to the halogenated nucleobase can form the compounds of the present teachings (referred to herein as "labeled nucleobase compound"). In some embodiments the acetylide anion does not comprise a label covalently attached. In the case where the acetylide anion does not comprise a label covalently attached thereto, the nucleobase compound conjugate can optionally be covalently attached to at least one label by contacting the nucleobase compound conjugate with at least one reagent capable of covalently attaching at least one label to the nucleobase compound conjugate to form a labeled nucleobase compound. Alternatively, in some embodiments the nucleobase compound conjugate can be covalently attached to one or more further linker elements prior to covalently attaching at least one label by contacting the nucleobase compound conjugate with one or more reagents capable of covalently attaching one or more further linker elements to the nucleobase compound conjugate. Alternatively, in some embodiments the nucleobase compound conjugate can be contacted with a reagent comprising one or more further linker elements and at least one label to form a labeled nucleobase compound conjugate.

In some embodiments, the nucleobase compound conjugate can optionally be activated and contacted with one or more further linker elements or a reagent comprising one or more further linker elements and at least one label. Alternatively, in some embodiments the one or more further linker elements or reagent comprising one or more further linker elements and at least one label to be covalently attached can optionally be activated contacted with an un-activated nucleobase compound conjugate. In some embodiments, the labeled nucleobase compound conjugate can optionally be contacted with at least one further linker and/or at least one further label. In the case where the labeled nucleobase compound conjugate is contacted with at least one further linker, the conjugate thus formed can optionally be contacted with at least one label to form a labeled nucleobase compound conjugate where the label comprises an energy transfer dye.

In some embodiments the halogenated nucleobase can be formed by a process comprising contacting a nucleobase compound with a reagent capable of covalently attaching a halogen to the methyl group of a nucleobase compound to form a halogenated nucleobase.

An exemplary synthesis is demonstrated in Scheme I. In the example, the 5'-hydroxyl group of a nucleobase compound, in this case 3' deoxythymidine (1), can be protected at the 5'-hydroxyl group by contacting the nucleobase compound with tetrabutyldimethylsilyl chloride (also known in the art as TBDMSCl or TBSCl) to form 5'-O-tert-butyldimethylsilyloxy-3'-deoxythymidine (2). The choice of protecting group on the 5'-hydroxyl need not be limited to TBDMS. One skilled in the art will readily appreciate that many possible hydroxyl protecting groups can be used. Examples of alternative protecting groups include but are not limited to trimethylsilyl (TMS), triisopropylsilyl (TIPS), tertbutyldiphenylsilyl (TBDPS), methoxymethyl (MOM), tetrahydropyran (THP), methoxyethoxymethyl (MEM), tert-butyl ether, benzyl ether, and the like. Further examples of hydroxyl protecting groups can be found in, for example, Green, T. W. & Wutts, P. G. M., *Protective Groups in Organic Synthesis*, 3rd Ed., John Wiley & Sons, Inc., 1999.

Next the methyl group on the 5'-O-tert-butyldimethylsilyloxy-3'-deoxythymidine (2) can be contacted with NBS under conditions that form 5'-O-tert-butyldimethylsilyloxy-5-bromomethyl-2',3'-dideoxyuridine (3) where the halogen atom can be covalently attached to the methyl group of the nucleobase compound. The halogenation of an alkyl group is well known in the art, and one of skill in the art will recognize that there are many reagents and conditions capable of forming a halogenated alkyl group. Examples of reagents known to be capable of covalently attaching a halogen to an alkyl group include but are not limited to $Br_2$, $Cl_2$, N-chlorosuccinimide (NCS), N-bromosuccinimide (NBS) or N-iodosuccinimide (NIS). Further examples can be found in, for example, Larock, R. C.; *Comprehensive Organic Transformations, A Guide to Functional Group Preparations*, VCH Publishers Inc, 1989.

For purposes of clarity, the term "dideoxyuridine" is used herein instead of "3' deoxythymidine" upon formation of a nucleobase compound conjugate (e.g., see compound (3) in scheme I below), consistent with the IUPAC recommendations for naming organic compounds as promulgated in *Nomenclature of Organic Chemistry*, Rigaudy, J. and Klesney, 10 S. P., Pergamon, 1979 [ISBN 0-08022-3699]; *A Guide to IUPAC Nomenclature of Organic Compounds (recommendations 1993)*, Panico, R.; Powell, W. H. and Richer, J-C., Blackwell Science, 1993 [ISBN 0-63203-4882]; Corrections published in *Pure Appl. Chem.*, 71 (7) 1327-1330 (1999).

Next, 5'-O-tert-butyldimethylsilyloxy-5-bromomethyl-2',3'-dideoxyuridine (3) can be coupled with an alkyne, in this case 3-(N-trifluoroacetyl-2-aminoethoxy)prop-1-yne, to form the 5'-O-tert-butyldimethylsilyloxy-(5-(4-(N-trifluoroacetyl-2-aminoethoxy)but-2-yn-1-yl))-2',3'-dideoxyuridine (4). It will be readily appreciated by one of skill in the art that the coupling of an alkyl halide with an alkyne can be carried out by a number of methods known in the art. Without being limiting in any way, one example of such a method known in the art is the so-called Castro-Stephens coupling, see for example, White, J. D., et. al. *J. Am. Chem. Soc.*, 123(23), 5407-5413 (2001) and Stephens, R. D., et. al. *J. Org. Chem.*, 28, 3313 (1963). For example, as shown in Scheme 1,5'-O-tert-butyldimethylsilyloxy-5-bromomethyl-2',3' dideoxyuridine (3) can be contacted with a mixture comprising a copper reagent, for example copper iodide (CuI), an alkyne, for example 3-(N-trifluoroacetyl-2-aminoethoxy)prop-1-yne, and a base, for example 1,8-diazobicyloclo[5.4.0]undec-7-ene (DBU), to form 5'-O-tert-butyldimethylsilyloxy-(5-(4-(N-trifluoroacetyl-2-aminoethoxy)but-2-yn-1-yl))-2',3'-dideoxyuridine (4), where an acetylide anion is formed in the mixture comprising CuI, 3-(N-trifluoroacetyl-2-aminoethoxy)prop-1-yne, and DBU.

A wide variety of copper reagents may be used in connection with the present teachings including but not limited to, copper iodide (CuI), copper bromide (CuBr), copper thiophenolate and copper cyanide (CuCN). Further examples of copper reagents can be found in, for example, Sigma-Aldrich catalogue. Similarly, a wide variety of bases can be used in connection with the present teachings.

The formation of the acetylide anion need not be limited to the mixture described above. The formation of acetylide anion is well known in the art, and further examples of reagents capable of forming an acetylide anion include, but are not limited to, lithium amide ($LiNH_2$), sodium amide ($NaNH_2$), alkyllithium reagents (e.g. methyl lithium, n-butyl lithium, t-butyl lithium), lithium diisopropyl amide (LiN(i-Pr)$_2$), Grignard reagents (e.g. ethyl magnesium bromide). In some embodiments, the acetylide anion can then be contacted with a halogenated nucleobase compound to form a propargyl-substituted nucleobase compound. In some embodiments the acetylide anion can be formed either prior to contact with the halogenated nucleobase compound or in the same reaction. In other words, the steps of contacting the alkyne with a reagent capable of forming an acetylide anion and contacting the acetylide anion with the halogenated nucleobase compound can occur serially, in discrete steps, or at the same time.

Next, the 5' hydroxyl protecting group on 5'-O-tert-butyldimethylsilyloxy-(5-(4-(N-trifluoroacetyl-2-aminoethoxy)but-2-yn-1-yl))-2',3'-dideoxyuridine (4) can be removed by contacting (4) with, for example, tetrabutylammonium fluoride (TBAF) to form 5-(4-(N-trifluoroacetyl-2-aminoethoxy)but-2-yn-1-yl)-2',3'-dideoxyuridine (5). The deprotection reagent need not be limited to TBAF. In fact, the deprotection reagent can be any reagent known in the art that is capable of removing a silyl protecting group. Furthermore, in some embodiments where the protecting is other than a silyl protecting group, the deprotection reagent can be any reagent known in the art capable of removing the protecting group of that embodiment. Further examples of hydroxyl protecting groups and deprotection reagents can be found in, for example, Green, T. W. & Wutts, P. G. M., *Protective Groups in Organic Synthesis*, $3^{rd}$ Ed., John Wiley & Sons, Inc., 1999.

Without being limiting in any way, monophosphate (6) can optionally be formed by treatment of 5-(4-(N-trifluoroacetyl-2-aminoethoxy)but-2-yn-1-yl)-2',3' dideoxyuridine (5) with, for example, POCl$_3$. 5-(4-(N-trifluoroacetyl-2-aminoethoxy)but-2-yn-1-yl)-2',3'-dideoxyuridine-5'-monophosphate (6) can then optionally be treated with, for example, carbonyldiimidazole (CDI) followed by tetrabutylammonium pyrophosphate (TBAPP) under appropriate conditions to form 5-(4-(N-trifluoroacetyl-2-aminoethoxy)but-2-yn-1-yl)-2',3' dideoxyuridine-5'-triphosphate (7). It will be recognized by one of skill in the art that conversion of 5-(4-(N-trifluoroacetyl-2-aminoethoxy)but-2-yn-1-yl)-2',3' dideoxyuridine (5) to triphosphate (7) can be accomplished by any method known in the art.

Finally, the trifluoroacetyl protecting group on triphosphate (7) can be removed by contacting (7) with, for example, NH$_4$OH to form 5-(4-(2-aminoethoxy)but-2-yn-1-yl)2',3' dideoxyuridine triphosphate (8). It will be understood by one of skill in the art that the deprotection reagent for conversion of triphosphate (7) to 5-(4-(2-aminoethoxy)but-2-yn-1-yl)-2',3' dideoxyuridine triphosphate (8) need not be limited to NH$_4$OH. In some embodiments, the amine-protecting group can be removed by any reagent known in the art capable of removing a trifluoroacetyl protecting group from an amine. Furthermore, the choice of protecting group need not be limited to TFA.

Scheme I

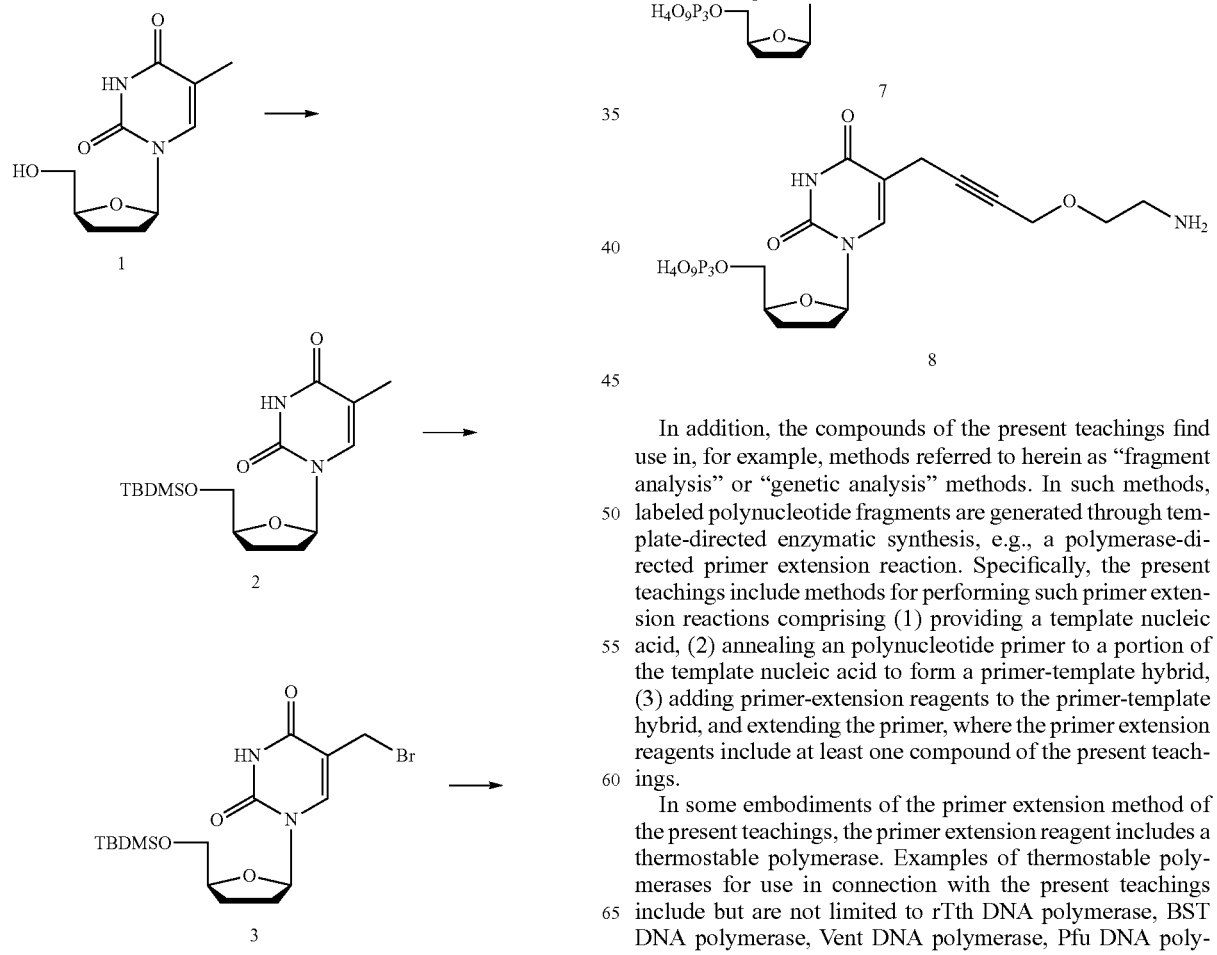

In addition, the compounds of the present teachings find use in, for example, methods referred to herein as "fragment analysis" or "genetic analysis" methods. In such methods, labeled polynucleotide fragments are generated through template-directed enzymatic synthesis, e.g., a polymerase-directed primer extension reaction. Specifically, the present teachings include methods for performing such primer extension reactions comprising (1) providing a template nucleic acid, (2) annealing an polynucleotide primer to a portion of the template nucleic acid to form a primer-template hybrid, (3) adding primer-extension reagents to the primer-template hybrid, and extending the primer, where the primer extension reagents include at least one compound of the present teachings.

In some embodiments of the primer extension method of the present teachings, the primer extension reagent includes a thermostable polymerase. Examples of thermostable polymerases for use in connection with the present teachings include but are not limited to rTth DNA polymerase, BST DNA polymerase, Vent DNA polymerase, Pfu DNA polymerase, or Taq polymerase enzyme as described in, for example, *PCR Primer: A Laboratory Manual*, Dieffenbach and Dveksler, eds., CSHL Press (1995). In some embodiments, the thermostable polymerase can be Taq DNA polymerase, or a mutant Taq polymerase enzyme having, for example, a mutation at the F667 position as described in, for example, Tabor and Richardson, EP 0 655 506. In some embodiments, the mutation at the F667 position can be F667Y. In an additional embodiment of the primer extension reaction of the present teachings, the Taq polymerase enzyme can be a mutant that includes, in addition to the F667Y mutation, one or more mutations at the 660, 664, 665 and/or the 681 positions. See U.S. patent application Ser. No. 09/041,878, filed Mar. 12, 1998, now U.S. Pat. No. 6,265,193. In some embodiments, representative mutations at the 660, 664, 665 and/or the 681 positions include, but are not limited to, R660D, R660E, R660C, R660S, R660P, and E681G. In some embodiments, the mutant Taq polymerase enzyme includes at least one the mutations R660C or R660S, R660P and F667Y.

Subsequent to a primer extension reaction, the fragments may be subjected to a size-dependent separation process. Without being limiting in any way, the size-dependent separation process can be by any one of electrophoresis, chromatography, or hybridization to a set of polynucleotide probes that bind to the fragments in a sequence-dependent manner as described in, for example, Drmanac et al., *Nature Biotechnology*, 16: 54-58 (1998), Ramsay, *Nature Biotechnology*, 16: 40-44 (1998) and U.S. Pat. No. 5,202,231. In some embodiments, subsequent to separation or hybridization, the fragments are detected, by, for example, laser-induced fluorescence. Further, in some embodiments, multiple classes of polynucleotides can be separated or hybridized simultaneously and the different classes can be distinguished by a set of spectrally resolvable labels.

In some embodiments of fragment analysis methods of the present teachings, classes identified in accordance with the present teachings can be defined in terms of terminal nucleotides so that a correspondence can be established between the four possible terminal bases and the members of a set of spectrally resolvable labels. When spectrally resolvable fluorescent labels are to be used, the dye set can be readily assembled by measuring the emission and absorption bandwidth of the dyes using commercially available spectrophotometers and then selecting a set of dyes with the desired spectral properties. In some embodiments, the classes arise in the context of the chemical or chain termination methods of DNA sequencing, and most preferably the classes arise in the context of the chain termination methods such as dideoxy DNA sequencing or Sanger-type sequencing.

Sanger-type sequencing involves the synthesis of a DNA strand by a DNA polymerase in vitro using a single-stranded or double-stranded DNA template whose sequence is to be determined. Synthesis is initiated at a defined site based on where an polynucleotide primer anneals to the template. The synthesis reaction is terminated by incorporation of a nucleotide analog that will not support continued DNA elongation. Exemplary chain-terminating nucleotide analogs include the 2',3'-dideoxynucleoside 5'-triphosphates (ddNTPs) which lack a 3'-OH group necessary for 3' to 5' DNA chain elongation. When proper proportions of dNTPs (2'-deoxynucleoside 5'-triphosphates) and one of the four ddNTPs are used, enzyme-catalyzed polymerization will be terminated in a fraction of the population of chains at each site where the ddNTP is incorporated. If fluorescently labeled primers or labeled ddNTPs are used for each reaction, the sequence information can be detected by fluorescence after separation by high-resolution electrophoresis. In the chain termination method, nucleotides of the present teachings can be used to form labeled dideoxynucleotides.

The primer-extension fragments can be subjected to a size-dependent separation process. For example the primer-extension fragments can be separated by electrophoretic procedures such as those described in, for example, Gould and Matthews, cited above; *Gel Electrophoresis of Nucleic Acids: A Practical Approach*, Rickwood and Hames, Eds., IRL Press Limited, London, 1981; *Methods of Protein and Nucleic Acid Research Vol.* 1, Osterman, Springer-Verlag, Berlin, 1984; or U.S. Pat. Nos. 5,374,527, 5,624,800 and 5,552,028. In some embodiments, the electrophoretic matrix can be crosslinked or uncrosslinked polyacrylamide having a concentration (weight to volume) of between about 220 weight percent. In some embodiments, the polyacrylamide concentration can be between about 4-8 percent. It will be understood that the range between about 2-20 weight percent also includes ranges including values of 3, 4, 5, 6, 7, 8, 9, 10, 11, 12, 13, 14, 15, 16, 17, 18 and 19. In some embodiments, in the context of DNA sequencing, the electrophoresis matrix can include at least one denaturing agent. The denturing agent need not be limited in any way, and can be any denaturing agent known in the art. Examples of denaturing agents include but are not limited to urea, formamide, and the like. Detailed procedures for constructing such matrices are given by Maniatis et al., *Methods in Enzymology*, 65, 299-305 (1980); Maniatis et al., *Biochemistry*, 14, 3787-3794 (1975); Maniatis et al., *Molecular Cloning: A Laboratory Manual*, Cold Spring Harbor Laboratory, New York, pgs. 179-185 (1982), and *ABI PRISM™ 377 DNA Sequencer User's Manual. Rev. A*, January 1995, Chapter 2 (p/n 903433, Applied Biosystems, Foster City, Calif.). The optimal electrophoresis conditions, e.g., polymer concentration, pH, temperature, concentration of denaturing agent, employed in a particular separation depends on many factors, including the size range of the nucleic acids to be separated, their base compositions, whether they are single stranded or double stranded, and the nature of the classes for which information is sought by electrophoresis. Accordingly application of the present teachings may require standard preliminary testing to optimize conditions for particular separations.

Subsequent to electrophoretic separation, the labeled polynucleotide fragments are detected, e.g., by measuring the fluorescence emission. Exemplary fluorescence-based electrophoresis detection systems are described elsewhere, e.g., U.S. Pat. Nos. 5,543,026; 5,274,240; 4,879,012; 5,091,652 and 4,811,218.

Some embodiments of the present teachings provide a method for polynucleotide sequencing by generating labeled nucleic acid fragments that are complimentary to a target sequence, then separating the labeled fragments, then detecting the labeled fragments. In some embodiments the labeled nucleic acid fragments comprise a terminator nucleic acid having a nucleobase disposed between a sugar or a sugar analog and a propargylic moiety. In some embodiments the nucleobase can be selected from a pyrimidine nucleobase or a pyrimidine nucleobase analog. In some embodiments the propargylic moiety can be covalently attached to the nucleobase at one of the C-3, C-4, C-5 or C-6 position of the nucleobase. In some embodiments the sugar or sugar analog is covalently attached to the nucleobase at the N-1 position of the nucleobase. And in some embodiments the propargylic moiety can include a propargyl group covalently attached to the nucleobase at the methylene carbon of the propargyl group, a linker covalently attached to the acetylene carbon of the propargyl group, and a label covalently attached to the linker.

Some embodiments of the present teachings provide a method of extending a polynucleotide primer comprising forming a hybridization complex between a 3'-extendable polynucleotide and a complementary sequence in a polynucleotide, and extending the 3'-extendable polynucleotide in the presence of a) a nucleotide 5'-triphosphate comprising a nucleobase disposed between a sugar or a sugar analog and a propargylic moiety, wherein the nucleobase is selected from a pyrimidine nucleobase or a pyrimidine nucleobase analog, the propargylic moiety is covalently attached to the nucleobase at the C-5 position of the nucleobase, the sugar or sugar analog is covalently attached to the nucleobase at the N-1 position of the nucleobase, the sugar or sugar analog is substituted by a triphosphate group, and the propargylic moiety comprises i) a propargyl group covalently attached to the nucleobase at the methylene carbon of the propargyl group, ii) a detectable label, and iii) a linker covalently linking the acetylene carbon of the propargyl group to the detectable label, and b) a template-dependent nucleic acid polymerase under conditions effective to append said nucleotide 5' triphosphate to the 3'-end of the extendable polynucleotide.

In some embodiments the extending can be performed in the presence of 4 nucleotide triphosphates and a non-extendable nucleotide triphosphate comprising a compound of the present teachings.

The preceding description is not intended to limit the present teachings to the embodiments described therein. On the contrary, the present teachings are intended to cover all alternatives, modifications, and equivalents readily apparent to one of skill in the art.

The present teachings will be further clarified by a consideration of the following examples, which are intended to be purely exemplary and are not intended to be limiting in any way.

Materials and Methods

Anhydrous N,N-dimethyl formamide (DMF), anhydrous carbon tetrachloride ($CCl_4$), anhydrous tetrahydrofuran (THF), and anhydrous methanol ($CH_3OH$) were used as received from Aldrich. 2'-Deoxythymidine was purchased from Barry and Associates, INC. Tetrabutylammonium pyrophosphate (TBAPP) was purchased from Sigma. Diisopropylethylamine (DIPEA), tert-Butyldimethylsilyl chloride (TB-DMSCl), imidazole, N-bromosuccinimide (NBS), tetrabutylammonium fluoride (TBAF), 1,8-diazabicyclo[5,4,0]undec-7-ene (DBU), copper iodide (CuI), phosphorus oxychloride ($POCl_3$), trimethyl phosphate, and tributylamine were used as received from, Sigma-Aldrich Co. (Milwaukee, Wis.).

Analytical thin layer chromatography (TLC) was conducted on aluminum sheets coated with 200 μm layer of silica gel 60 $F_{254}$ (Merck). Flash column chromatography was performed with silica gel 60, 230-400 mesh (Merck). Compounds were detected by UV light (254 nm). $^1H$, $^{31}P$, and $^{19}F$ NMR were taken on a Varian XL-300 spectrometer at 300 MHz, at 121.4 MHz, and 282.2 MHz, respectively. Chemical shifts are recorded in parts per million with the solvent as internal standard. Listed J values in $^1H$ NMR spectra data refer to proton-proton couplings. $^{31}P$ NMR spectra were referenced to external 85% phosphoric acid. UV absorption spectra were determined on a Beckman DU-70 spectrophotometer. Mass spectra were determined on a Perceptive Biosystems Voyager 1100 series MALDI-TOF, matrix, 3-Hydroxypicolinic acid. The HPLC systems used for analytical and preparative purposes were as follows:

Analytical reverse-phase HPLC: column: Eclipse XAD-C8, 5 μm particle size, 4.6×150 mm; gradient: 5% acetonitrile and 95% 0.1 M triethylammonium acetate (TEAA) at 1.5 mL/min over 3 min and then 5 to 50% acetonitrile and 95 to 50% 0.1 M TEAA at 1.5 mL/min over 20 min, followed by 100% acetonitrile at 1.5 mL/min over 3 min. Detector: Perkin-Elmer UV/Vis Detector LC 295 and Perkin-Elmer Florescence detector LC 240 equipped with a Perkin-Elmer series 200 liquid chromatography pump.

Analytical ion exchange HPLC: column: Aquapore AX-300, 7 μm particle size, 4.6×220 mm; gradient: 40% acetonitrile and 60% 0.1 M triethylammonium bicarbonate (TEAB) at 1.5 mL/min over 3 min, followed by 40% acetonitrile and 60% 1.5 M TEAB at 1.5 mL/min over 20 min. Detector: Applied Biosystems 785 A programmable Absorbance Detector and Perkin-Elmer Florescence detector LC 240 equipped with Perkin-Elmer series 410 BIO LC pump.

Preparative reverse phase HPLC: column: Prep Nova Pak HR-C18, 6 μm particle size, 60 pore size, 40×300 (waters Division of Milipore corporation p/n WAT037704); gradient: 5% acetonitrile and 95% 0.1 M triethylammonium acetate (TEAA) at 4.5 mL/min over 3 min and then 5 to 50% acetonitrile and 95 to 50% 0.1 M TEAA at 4.5 mL/min over 20 min, followed by 100% acetonitrile at 4.5 mL/min over 3 min. Detector: Waters PrepLC 4000 systems equipped with Waters 490 E programmable Multiwavelength Detector.

Synthesis of 5'-O-tert-butyldimethylsilyloxy-3'-deoxythymidine (2)

To a stirred solution of 3'-deoxythymidine (2.0 g, 8.84 mmol) in anhydrous DMF (15 mL) were added imidazole (0.90 g, 13.26 mmol) and tert-butyldimethylsilyl chloride (TBDMSCl) (1.73 g, 11.49 mmol) at r.t., followed by stirring for 4 h. After evaporating the solvent, the residue was partitioned between $CH_2Cl_2$ and water. The organic layer was dried over $Na_2SO_4$ and evaporated to dryness. The organic residue was purified by silica gel column chromatography with $MeOH/CH_2Cl_2$ (0-3%) to give the corresponding product (2.60 g, 7.63 mmol, 87%). $^1H$ NMR ($CDCl_3$, 300 MHz) δ 8.80 (br s, 1H, NH), 7.57 (q, 1H, $H_6$, J=1.2 Hz), 6.07 (dd, 1H, $H_{1'}$, J=4.8 and 6.3 Hz), 4.10-4.18 (m, 1H, $H_{4'}$), 3.98 (dd, 1H, $H_{5'}$, J=2.4 and 11.4 Hz), 3.70 (dd, 1H, $H_{5'}$, J=3.0 and 11.4 Hz), 2.30-2.4 (m, 1H, $H_{2'}$), 1.93-2.04 (m, 3H, $H_{2'}$, and $2H_{3'}$), 1.91 (d, 9H, 3 $CH_3$), 0.10 (2 s, 6H, 2 $CH_3$).

Synthesis of 5'-O-tert-butyldimethylsilyloxy-5-bromomethyl-2',3'-dideoxyuridine (3) and 5'-O-tert-butyldimethylsilyloxy-(5-(4-(N-trifluoroacetyl-2-aminoethoxy)but-2-yn-1-yl))-2',3'-dideoxyuridine (4)

A solution of 5'-O— tert-butyldimethylsilyl-2'-deoxythymidine (500 mg, 1.47 mmol) in $CCl_4$ (50 mL) was treated with N-bromosuccinimide (NBS) (376 mg, 2.20 mmol), followed by irradiation from a flood lamp (150 W) under reflux for 2-3 h. After filtering the solid, the filtrate was evaporated to dryness, followed by coevaporating with THF (20 mL×3) to give 3. To a stirred solution of the 3-{2-(trifluoroacetamido)ethoxy}propyne (530.9 mg, 2.94 mmol), DBU (430.4 μL, 2.94 mmol) and CuI (559 mg, 2.94 mmol) in THF (15 mL) was added a solution of 3, followed by stirring at r.t for 18 h. After evaporating solvent, the residue was purified by silica gel column chromatography with $MeOH:CH_2Cl_2$ (0-3%) to afford the corresponding product 4 (90 mg, 0.17 mmol, 12%) over two steps. $^1H$ NMR ($CDCl_3$, 300 MHz) δ 9.12 (br s, 1H, NH), 7.72 (t, 1H, $H_6$, J=1.2 Hz), 7.00 (br s, 1H, NH), 6.03 (dd, 1H, $H_{1'}$, J=3.9 and 6.6 Hz), 4.24-4.12 (m, 3H, $H_{4'}$, $CH_2$), 3.90

(dd, 1H, H$_{5'}$, J=3.6 and 11.4 Hz), 3.76 (dd, 1H, H$_{5'}$, J=3.9 and 11.4 Hz), 3.70-3.54 (m, 4H, 2 CH$_2$), 2.48-2.34 (m, 1H, H$_{2'}$), 2.09-1.90 (m, 3H, H$_{2'}$, 2 H$_{3'}$), 0.90 (d, 9H, 3 CH$_3$), 0.09 (s, 6H, 2 CH$_3$).
$^{19}$F NMR (CDCl$_3$, 282.2 MHz) δ −76.34 (s, CF$_3$). Mass spectrum: 534.5 (M$^+$+H, C$_{23}$H$_{34}$F$_3$N$_3$O$_6$Si).

Synthesis of 5-(4-(N-trifluoroacetyl-2-aminoethoxy)but-2-yn-1-yl)-2',3'-dideoxyuridine (5)

To a solution of 4 (90.0 mg, 0.17 mmol) in THF (5 mL) was added 1.0 M tetrabutylammonium fluoride (TBAF, 0.2 mL, 0.19 mmol), which was stirred at r.t. for 3 h. After evaporating solvent, the organic residue was purified by silica gel column chromatography with MeOH/CH$_2$Cl$_2$ to give the product 5 (30 mg, 0.074 mmol, 43%). $^1$H NMR (CDCl$_3$, 300 MHz) δ 8.01 (t, 1H, H$_6$, J=1.2 Hz), 6.08 (dd, 1H, H$_{1'}$, J=3.6 and 6.6 Hz), 4.23 (t, 2H, CH$_2$), 4.20-4.10 (m, 1H, H$_{4'}$), 3.85 (dd, 1H, H$_{5'}$, J=3.3 and 11.4 Hz), 3.75-3.63 (m, 3H, H$_{5'}$, CH$_2$), 3.50-3.45 (m, 2H, CH$_2$), 3.30-3.25 (m, 2H, CH$_2$), 2.47-2.34 (m, 1H, H$_{2'}$), 2.15-1.80 (m, 3H, H$_{2'}$, 2 H$_{3'}$). $^{19}$F NMR (CDCl$_3$, 282.2 MHz) δ −77.79 (s, CF$_3$).
Mass spectrum: 420.5 (M$^+$+H, C$_{17}$H$_{20}$F$_3$N$_3$O$_6$).

Synthesis of 5-(4-(2-aminoethoxy)but-2-yn-1-yl)-2',3' dideoxyuridine triphosphate (8)

To a solution of 5 (30 mg, 0.0738 mmol) in P(O)(OCH$_3$)$_3$ (0.5 mL) was treated with POCl$_3$ (70 μL, 0.73 mmol) at 0° C., followed by stirring at r.t for 2-3 h and then evaporating solvent under reduced pressure and purification by preparative reverse phase HPLC to afford the corresponding mono phosphate 6. $^{31}$P NMR (CD$_3$OD, 121.4 MHz) δ 0.79 (s); $^{19}$F NMR (CDCl$_3$, 282.2 MHz) δ −77.37 (s, CF$_3$). To a dried solution of 6 in DMF (1 mL) were added 1,1'-carbonyldiimidazole (CDI, 33 mg, 0.21 mmol), followed by stirring at r.t. for 5 h and then quenching with MeOH (8 μL, 0.21 mmol). A solution of tetrabutylammonium pyrophosphate (TBAPP, 143.0 mg, 0.33 mmol) and tributyl amine (0.15 mL, 0.66 mmol) in DMF (1.5 mL) was added to the above solution at r.t. under Ar, followed by stirring overnight and then quenched with 2.0 M TEAB. After evaporating solvent, the organic residue was purified by preparative reverse phase HPLC with 100 mM TEAA/AcCN (0 to 50% gradient) to give the corresponding triphosphate 7. $^1$H NMR (D$_2$O, 300 MHz) δ 7.74 (s, 1H, H$_6$), 5.95 (dd, 1H, H$_{1'}$, J=3.3 and 6.3 Hz), 4.29-4.20 (m, 1H, H$_{4'}$), 4.18-4.07 (m, 3H, CH$_2$ and H$_{5'}$), 4.02-3.92 (m, 1H, H$_{5'}$), 3.58 (t, 2H, CH$_2$, J=5.1 Hz), 3.38 (t, 2H, CH$_2$, J=5.1 Hz), 3.20 (s, 2H, CH$_2$), 2.35-2.22 (m, 1H, H$_2$), 2.10-1.92 (m, 3H, H$_2$, and 2H$_{3'}$). $^{31}$P NMR (D$_2$O, 121.4 MHz) δ −10.52 (d, J=19.2 Hz), −10.95 (d, J=20.3 Hz), −22.96 (t, J=20.3 Hz); $^{19}$F NMR (D$_2$O, 282.2 MHz) δ −76.37 (s, CF$_3$). Removal of trifluoro acetate (TFA) protecting group was accomplished by treatment with NH$_4$OH (33%, 500 μL) at 60° C. for 20 min and then at r.t for 1 h to give the corresponding triphosphate 8 (17 mM, 500 μL).

Synthesis of Compound (10)

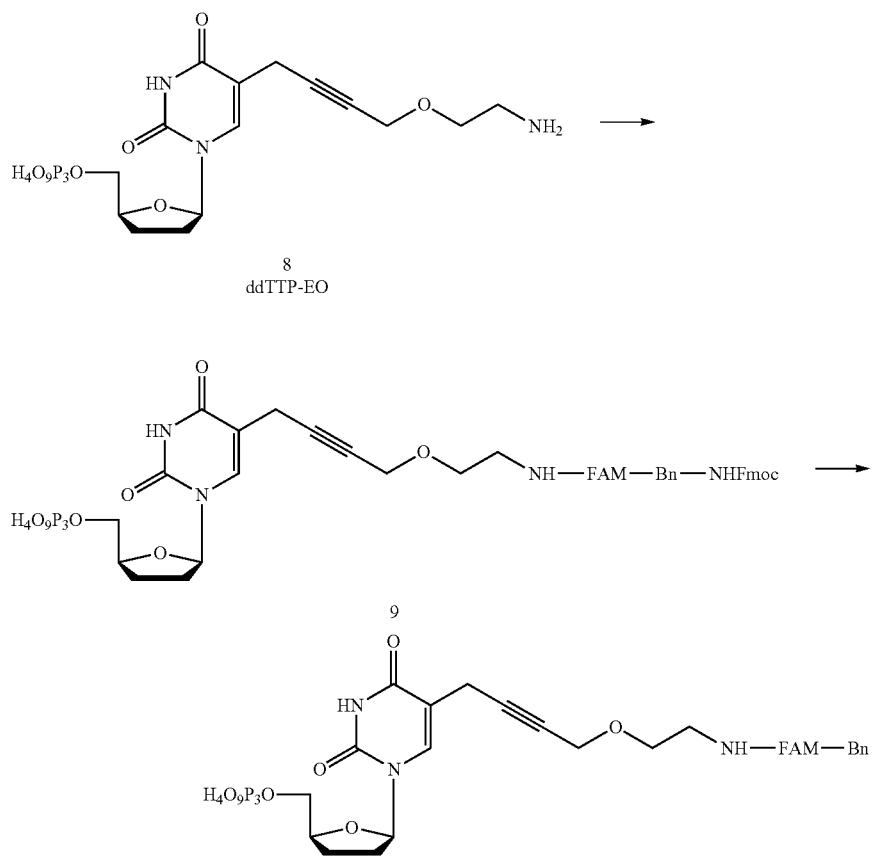

To a solution of 8 (17 mM, 20 μL) in NaHCO₃ (100 μL) was added a solution of N—(N-(9-fluorenylmethoxycarbonyl)-4-aminomethylbenzoyl)-4'-aminomethyl-6-carboxyfluorescein N-hydroxysuccinimide (NHS) ester (1 mg/12 μL DMSO, 0.34 μmole), followed by storing in the dark for 2 h. The mixture was purified on ion exchange HPLC to give 9. Removal of the 9-fluorenylmethoxycarbonyl (Fmoc) group was accomplished by treatment with NH₄OH (aq), followed by purification on analytical reverse phase HPLC to give 10.

Synthesis of Compound (11)

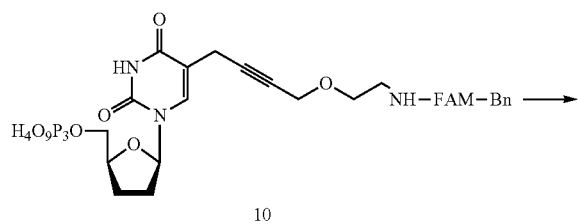

10

-continued

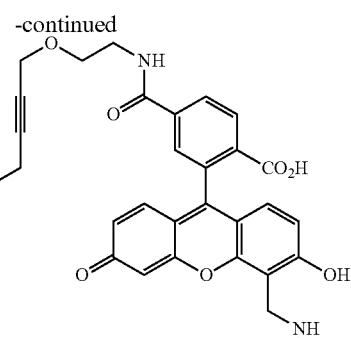

11

To a solution of dried 10 in NaHCO₃ (0.25 M, 50-80 μL) was added a solution of DTAMRA-1 NHS ester (7 μL, 1 mg/12 μL DMSO), followed by storing in the dark for 2 h. The mixture was purified on ion exchange HPLC and then analytical reverse phase HPLC to give 11 (185 μM, 120 μL).

Synthesis of 5-(4-(N-(4-aminomethylbenzoyl)-2-aminoethoxy)but-2-yn-1-yl)-2',3' dideoxyuridine triphosphate (13)

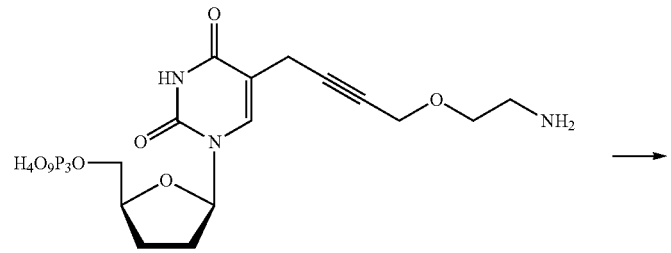

8

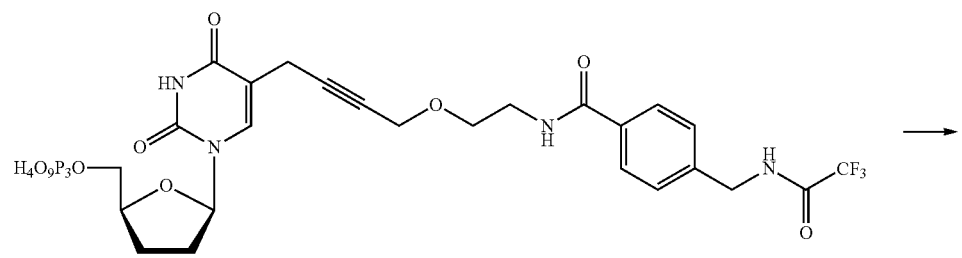

12

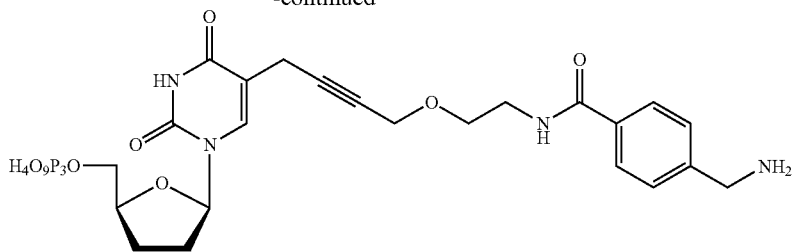

13

To a solution of 8 (17 mM, 20 μL) in formamide (85 μL) was added a solution of N-trifluoracetyl-4-aminomethyl-benzoate NHS ester (1 mg/12 μL DMSO, 0.3 μmole) and diisopropylethylamine (DIPEA, also known as DIEA) (20 μL), followed by storing in the dark for 2 h. The mixture was purified on ion exchange HPLC to give 12. Removal of TFA group was accomplished by treatment with NH$_4$OH (aq), followed by purification on analytical reverse phase HPLC to give 13.

Synthesis of Compound (15)

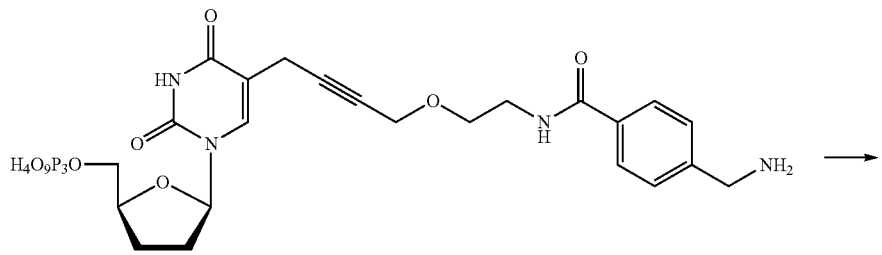

13

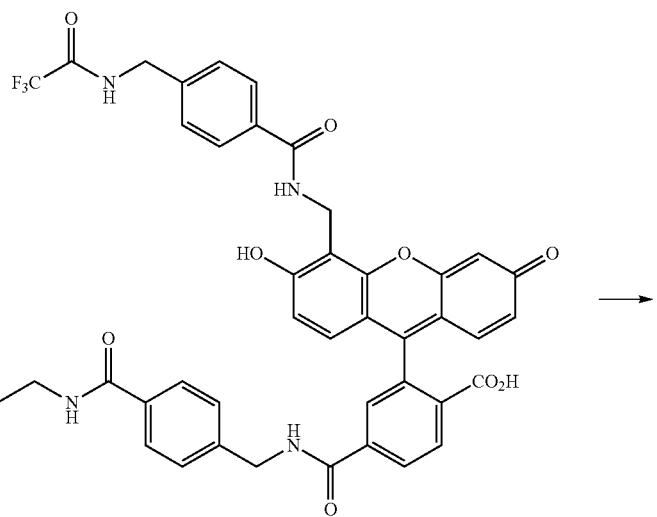

14

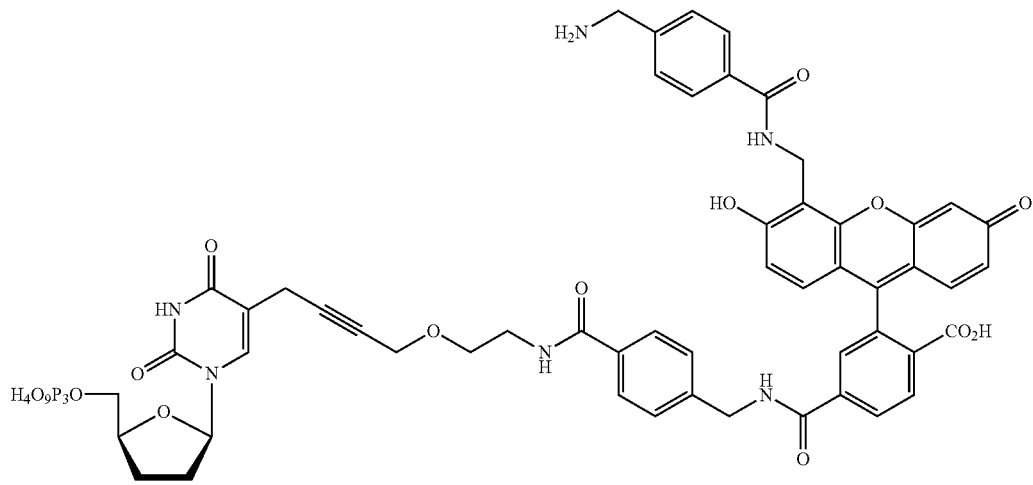

15

To a solution of 13 in NaHCO$_3$ (0.25 M, 80 μL) was added a solution of N—(N-(trifluoroacetyl)-4-aminomethylbenzoyl)-4'-aminomethyl-6-carboxy-fluorescein NHS ester (12 μL, 1 mg/12 μL DMSO), followed by storing in the dark for 15 h. The mixture was purified on ion exchange HPLC to give 14. A TFA group was removed by treatment with NH$_4$OH (aq), followed by purification on reverse phase HPLC to give 15.

Synthesis of Compound (16)

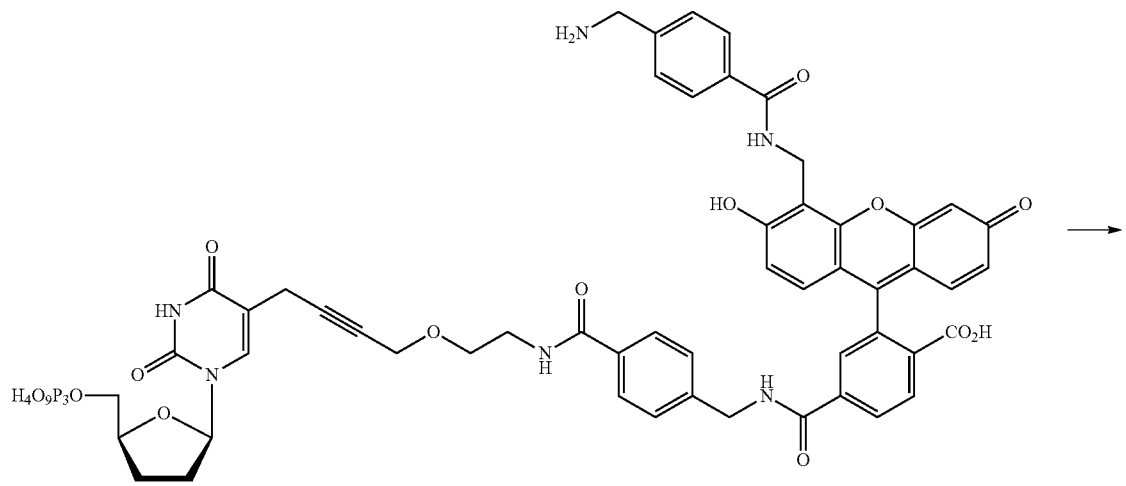

15

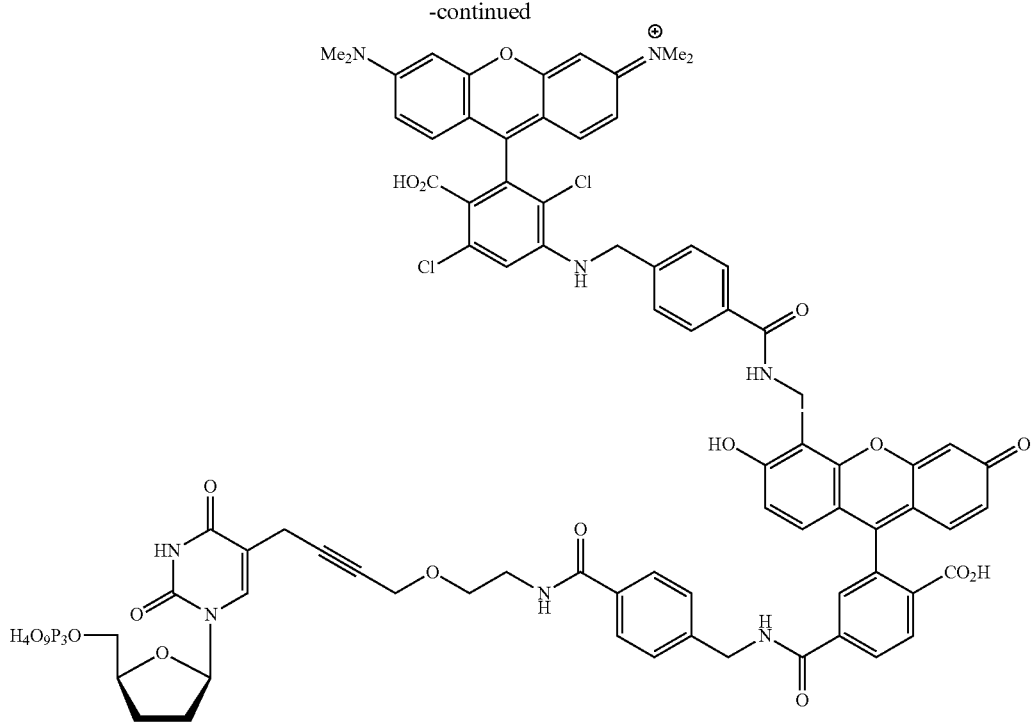

16

To a solution of dried 15, ddTTP-EO-Bn-Fam-Bn, in NaHCO₃ (0.25 M, 100 μL) was added a solution of dTAM-1 NHS ester (8 μL, 1 mg/12 μL DMSO), followed by storing in the dark for 2 h. The mixture was purified on reverse phase HPLC to give 16 (625 μM, 200 μL).

Synthesis of 5'-O-tert-butyldimethylsilyloxy-5-bromomethyl-2',3'-dideoxyuridine (3) and 5'-O-tert-butyldimethylsilyl-5-{4-(N-trifluoroacetylamino)but-2-yn-1-yl}-2',3'-dideoxyuridine (17)

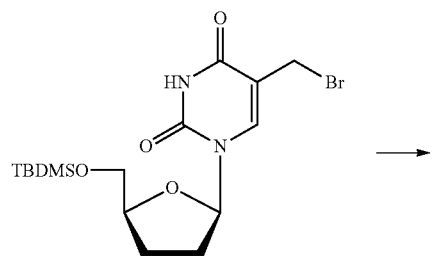

3

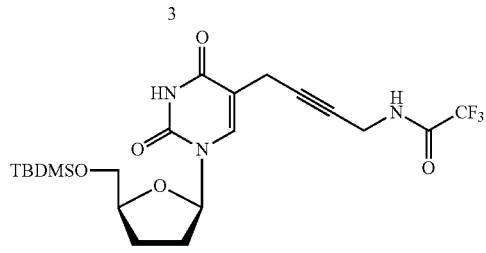

17

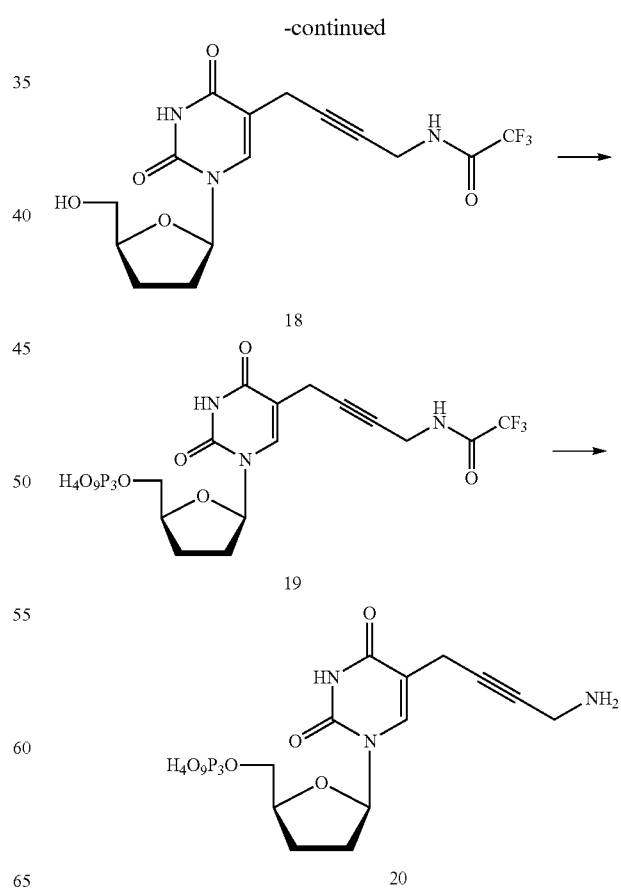

A solution of 5'-O-TBDMS-3'-deoxythymidine (2) (700 mg, 2.055 mmol) in CCl$_4$ (50 mL) was treated with NBS (702 mg, 4.11 mmol), followed by irradiation from a flood lamp (150 W) under reflux for 3 h to give (3). After filtering the solid, the filtrate was evaporated to dryness, followed by coevaporating with THF (20 mL×3). To a stirred solution of the 3-(trifluoroacetamido)prop-1-yne (620 mg, 4.11 mmol), DBU (0.61 mL, 4.11 mmol) and CuI (782 mg, 4.11 mmol) in THF (20 mL) was added a solution of 3 (Need conc. and solvent), followed by stirring at r.t for 15 h. After evaporating solvent, the residue was purified by silica gel column chromatography with MeOH:CH$_2$Cl$_2$ (0-4%) to afford 17 (170 mg, 0.35 mmol, 17%) over two steps. $^1$H NMR (CDCl$_3$), 300 MHz) δ 9.55 (br s, 1H, NH), 7.74 (s, 1H, H$_6$), 7.18 (br s, 1H, NH), 6.04 (dd, 1H, H$_{1'}$, J=3.9 and 6.3 Hz), 4.23-4.10 (m, 3H, H$_{4'}$ and CH$_2$), 3.94 (dd, 1H, H$_{5'}$, J=3.3 and 11.4 Hz), 3.75 (dd, 1H, H$_{5'}$, J=3.6 and 11.4 Hz), 3.26-3.22 (m, 2H, 2 CH$_2$), 2.45-2.35 (m, 1H, H$_{2'}$), 2.09-1.85 (m, 3H, H$_{2'}$, 2H$_{3'}$), 0.90 (d, 9H, 3 CH$_3$), 0.09 (s, 6H, 2 CH$_3$). $^{19}$F NMR (CDCl$_3$, 282.2 MHz) δ −76.22 (s, CF$_3$).

Synthesis of 5-{4-(trifluoroacetamido)butyn-1-yl}-2',3'-dideoxyuridine (18)

To a solution of 17 (170 mg, 0.347 mmol) in THF (5 mL) was added 1.0 M TBAF (0.38 mL, 0.381 mmol), which was stirred at r.t. for 4 h. After evaporating solvent, the organic residue was purified by silica gel column chromatography with MeOH/CH$_2$Cl$_2$ (0-4%) to give the product 18 (50 mg, 0.133 mmol, 38%). $^1$H NMR (DMSO-d$_6$, 300 MHz) δ 11.39 (s, 1H, NH), 9.89 (br s, 1H, NH), 7.84 (s, 1H, H$_6$), 5.96 (dd, 1H, H$_{1'}$, J=3.6 and 6.6 Hz), 5.03 (t, 1H, OH, J=5.4 Hz), 4.06-3.96 (m, 3H, H$_{4'}$ and CH$_2$), 3.38-3.49 (m, 2H, 2H$_{5'}$), 3.16 (br s, 2H, CH$_2$), 2.30-2.20 (m, 1H, H$_2$), 2.00-1.74 (m, 3H, H$_{2'}$, 2 H$_{3'}$). $^{19}$F NMR (CD$_3$OD, 282.2 MHz) δ −77.78 (s, CF$_3$). Mass spectrum: 375.1 (M$^+$+H, C$_{15}$H$_{16}$F$_3$N$_3$O$_5$).

Synthesis of 5-(4-aminobutyn-2-yl)-2',3'-dideoxyuridine-5'-triphosphate (20)

To a solution of 18 (30 mg, 0.0799 mmol) in P(O)(OCH$_3$)$_3$ (0.5 mL) was treated with POCl$_3$ (50 μL, 0.53 mmol) at 0° C., followed by stirring at r.t. for 5-6 h and then evaporating solvent under reduced pressure and purification by preparative reverse phase HPLC to afford the corresponding triphosphate 19. $^1$H NMR (D$_2$O, 300 MHz) δ 7.74 (s, 1H, H$_6$), 5.96 (dd, 1H, H$_{1'}$, J=3.3 and 6.6 Hz), 4.28-4.18 (m, 1H, H$_{5'}$), 4.16-4.10 (m, 1H, H$_{5'}$), 4.02-3.96 (m, 3H, H$_{4'}$ and CH$_2$), 3.17 (s, 2H, CH$_2$), 2.28-2.22 (m, 1H, H$_{2'}$), 2.05-1.98 (m, 3H, H$_{2'}$ and 2H$_{3'}$). $^{31}$P NMR (D$_2$O, 121.4 MHz) δ −10.50 (d, J=20.3 Hz), −10.80 (d, J=20.3 Hz), −22.90 (t, J=20.3 Hz); $^{19}$F NMR (D$_2$O, 282.2 MHz) δ −76.41 (s, CF$_3$). Removal of TFA protecting group was accomplished by treatment with NH$_4$OH (33%, 500 μL) at 60° C. for 20 min and then at r.t. for 1 h to give the corresponding triphosphate 20 (9.2 mM, 200 μL). Mass spectrum: 518.2 [M$^+$-H], C$_{13}$H$_{20}$N$_3$O$_{13}$P$_3$.

Synthesis of 5-{Bn-(4-aminobutyn-2-yl)}-2',3'-dideoxyuridine-5'-triphosphate (22)

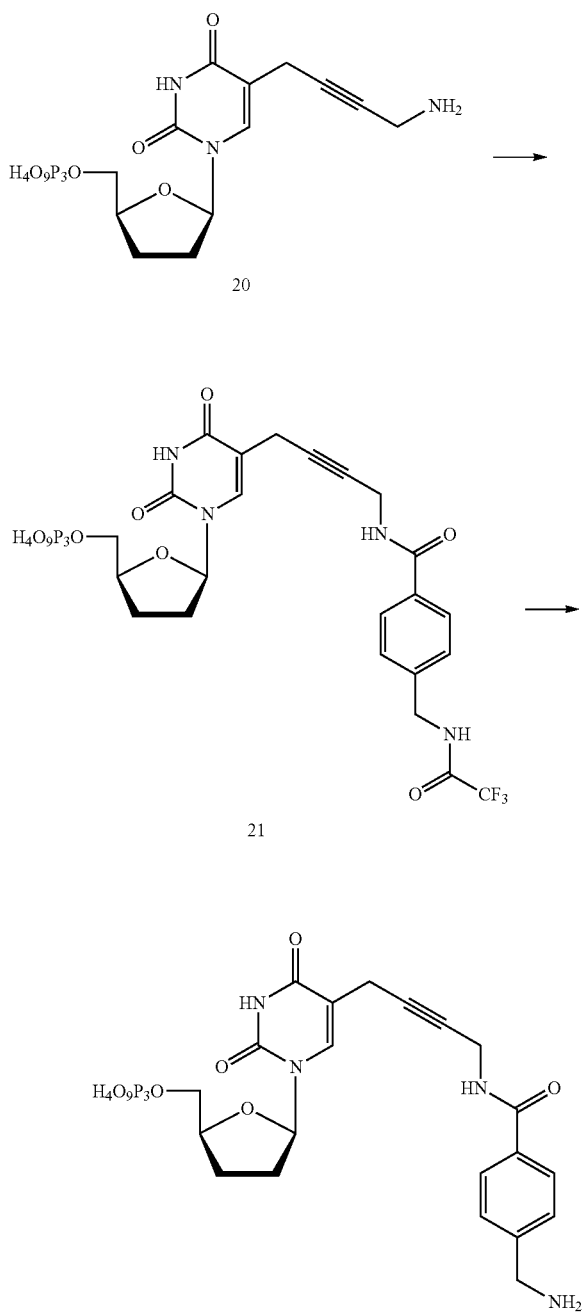

To a solution of 20 (9.2 mM, 50 μL) in formamide (100 μL) was added a solution of benzoyl NHS ester (1 mg/12 μL DMSO, 36 μL, 0.9 μmole) and DIEA (35 μL), followed by storing in the dark for 2 h. The mixture was purified on ion exchange HPLC to give 21. Removal of the TFA group was accomplished by treatment with NH$_4$OH (aq), followed by purification on analytical reverse phase HPLC to give 22.

Synthesis of Compound (24)

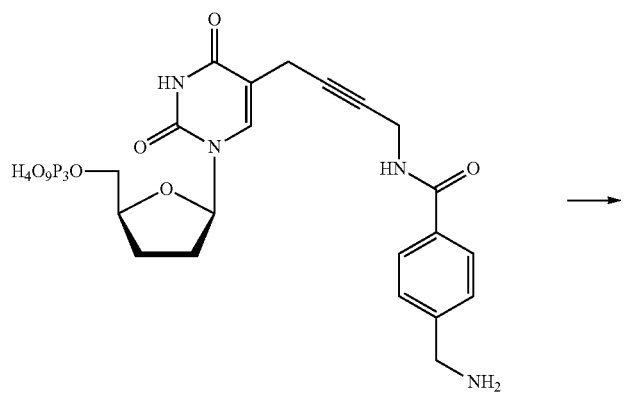

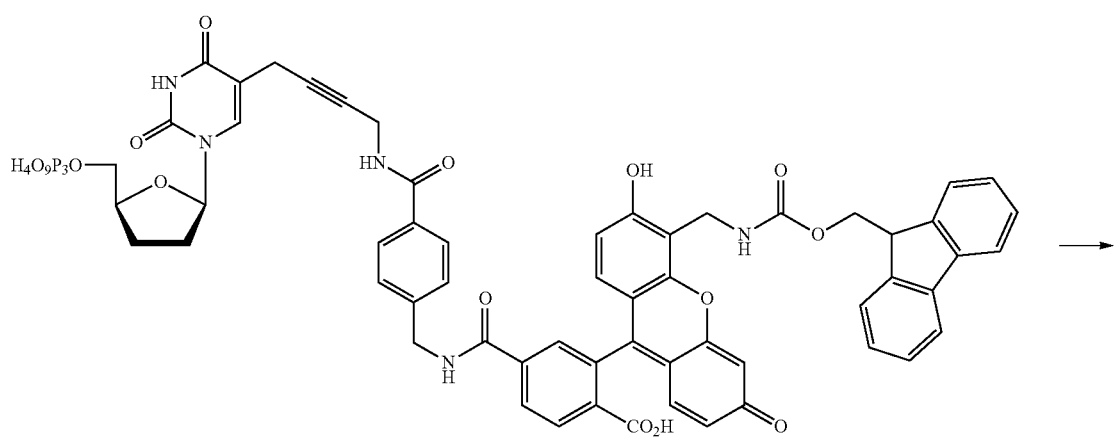

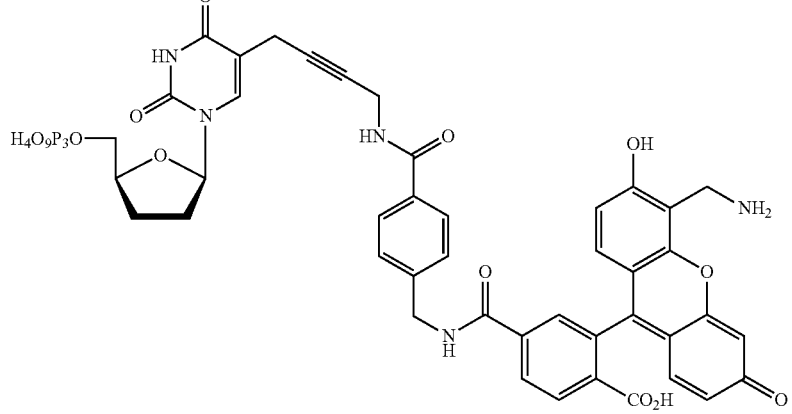

To a solution of 22 in NaHCO$_3$ (0.25 M, 80 μL) was added a solution of N—(N-(9-fluorenylmethoxycarbonyl)-4-aminomethylbenzoyl)-4'-aminomethyl-6-carboxy-fluorescein NHS ester (1 mg/12 μL DMSO, 6 μL), followed by storing in the dark for 2 h. The mixture was purified on ion exchange HPLC to give 23. The Fmoc group was removed by treatment with NH$_4$OH (aq), followed by purification on reverse phase HPLC to give 24.

Synthesis of Compound (25)
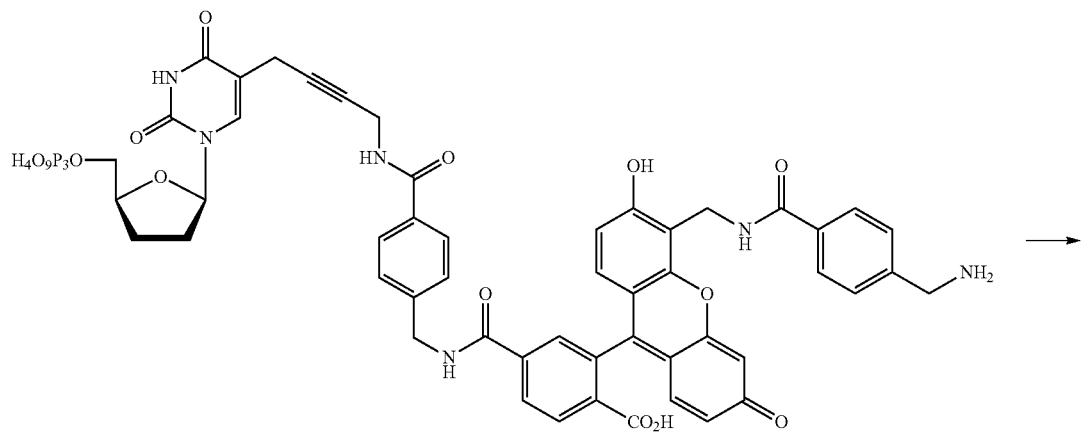
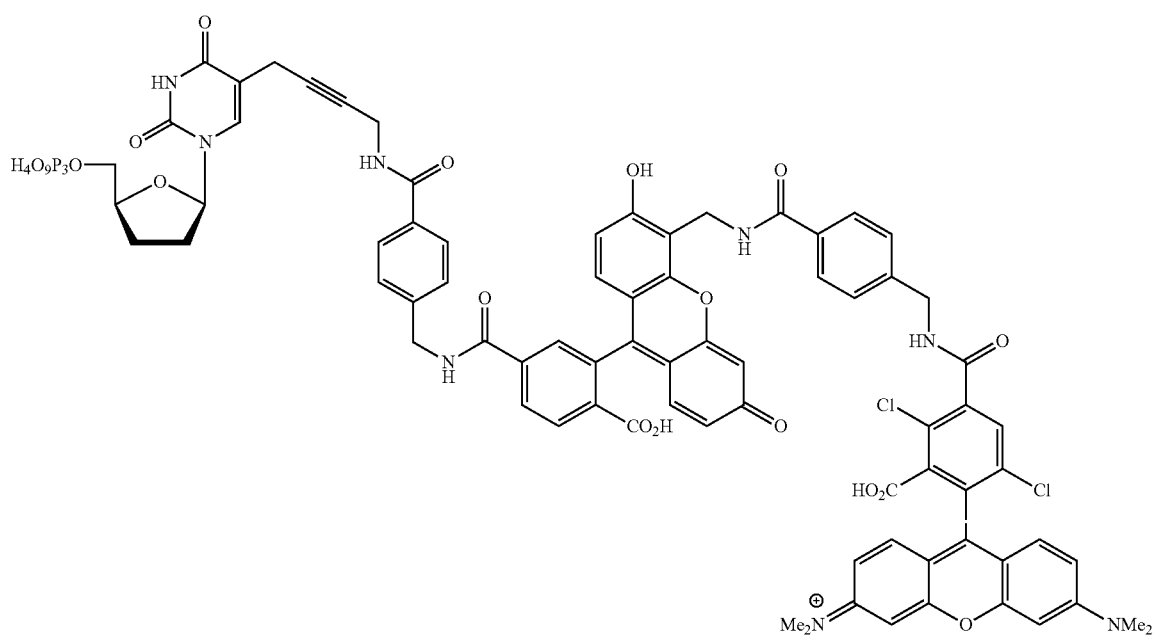
To a solution of dried 24 in NaHCO₃ (0.25 M, 150 μL) was added a solution of DTAMRA-2 NHS ester (4 μL, 1 mg/12 μL DMSO), followed by storing in the dark for 2 h. The mixture was purified on ion exchange HPLC and then analytical reverse phase HPLC to give 25.

Synthesis of Compound (27)

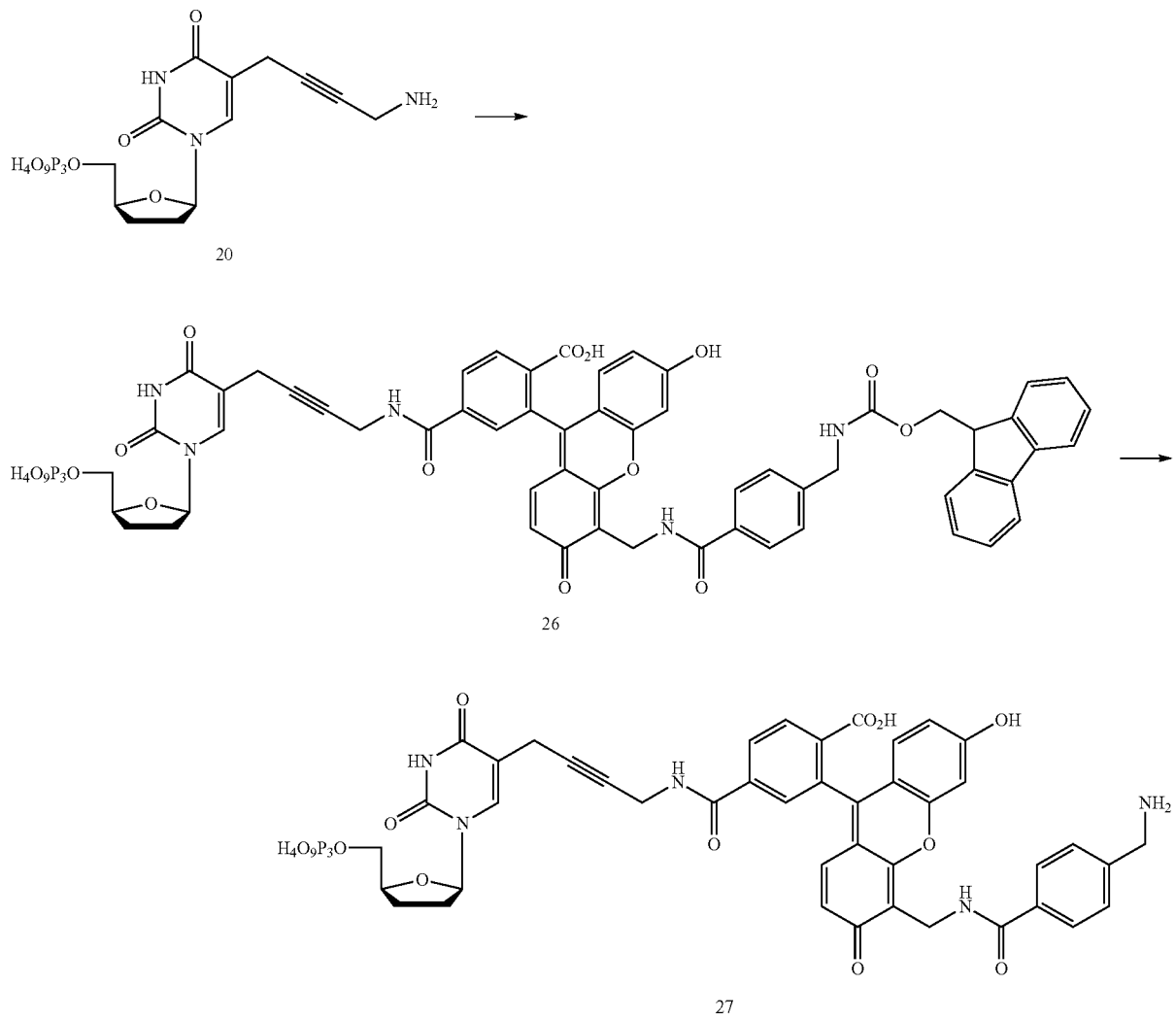

To a solution of ddTTP-PA (9.2 mM, 30 μL) 20 in NaHCO₃ (0.25 M, 70 μL) was added a solution of N—(N-(9-fluorenyl-methoxycarbonyl)-4-aminomethylbenzoyl)-4'-aminomethyl-6-carboxyfluorescein NHS ester (1 mg/12 μL DMSO, 10 μL, 0.28 μmole), followed by storing in the dark for 2 h. The mixture was purified on ion exchange HPLC to give the corresponding product 26 (ddTTP-PA-6-Fam-Bn-NHFmoc).

The Fmoc protecting group was removed by treatment with NH₄OH (33%, 500 μL) at 60° C. for 20 min and then at r.t. for 1 h, followed by purification on analytical reverse phase HPLC to give the compound 27.

Synthesis of Compound (28)

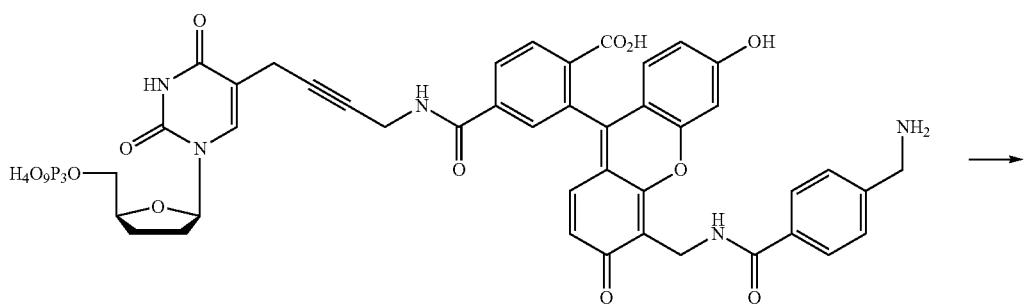

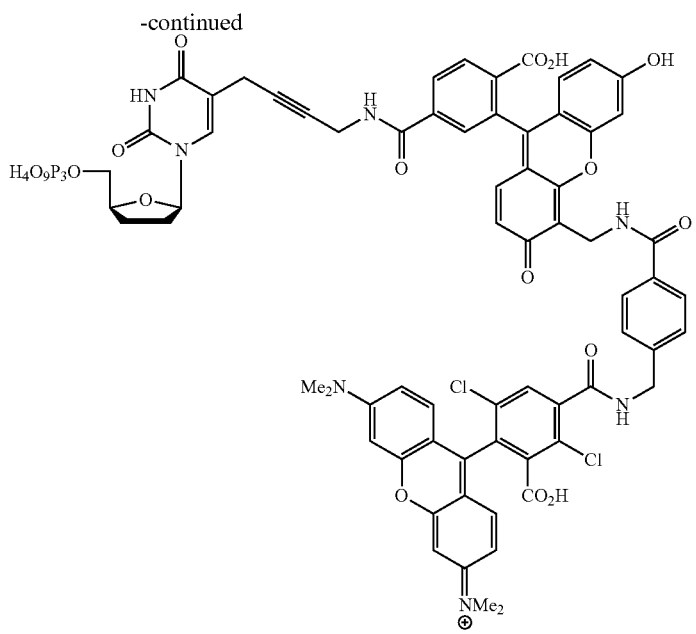

28

To a solution of dried 27 in NaHCO₃ (0.25 M, 50-80 µL) was added a solution of DTAMRA-2 NHS ester (7 µL, 1 mg/12 µL DMSO), followed by storing in the dark for 2 h. The mixture was purified on ion exchange HPLC and then analytical reverse phase HPLC to give 28 (90 µM, 300 µL).

Synthesis of Compound (29)

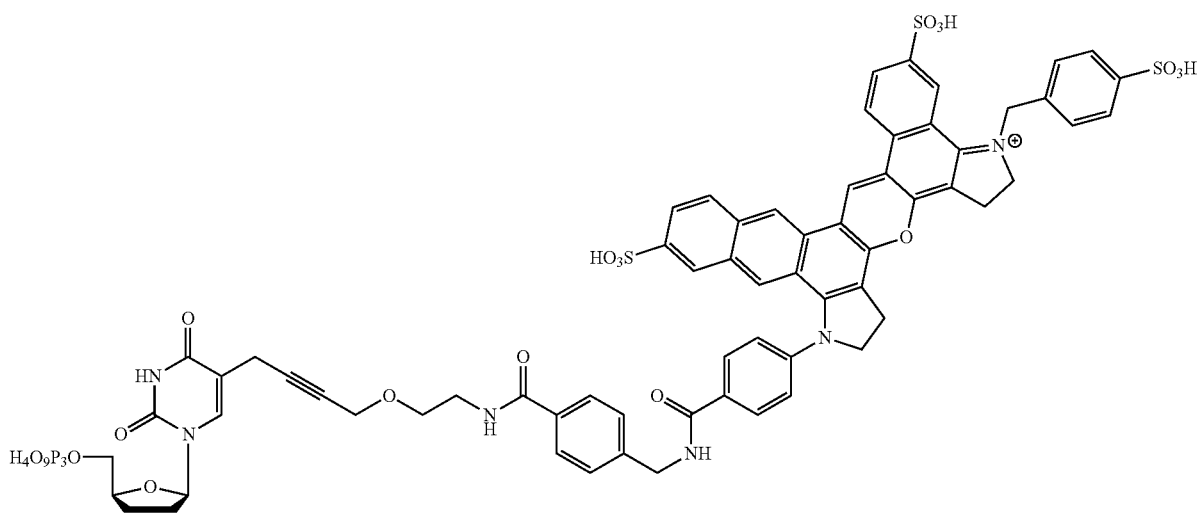

29

To a solution of 13, ddTTP-PA-Bn (9.2 µM, 10 µL) in NaHCO₃ (0.25 M, 50 µL) was added a solution of SNJ3 NHS ester (e.g. see Examples 19 and 13 in U.S. Pat. No. 6,583,168 for synthesis of the dye carboxylic acid compound 115 and conversion to an NHS ester, respectively) (1 mg/12 µL DMSO, 4 µL), followed by storing in the dark for 3 h. The mixture was purified on ion exchange HPLC and analytical reverse phase HPLC to give the corresponding product 29 (10 µM, 100 µL).

Synthesis of Compound (30)

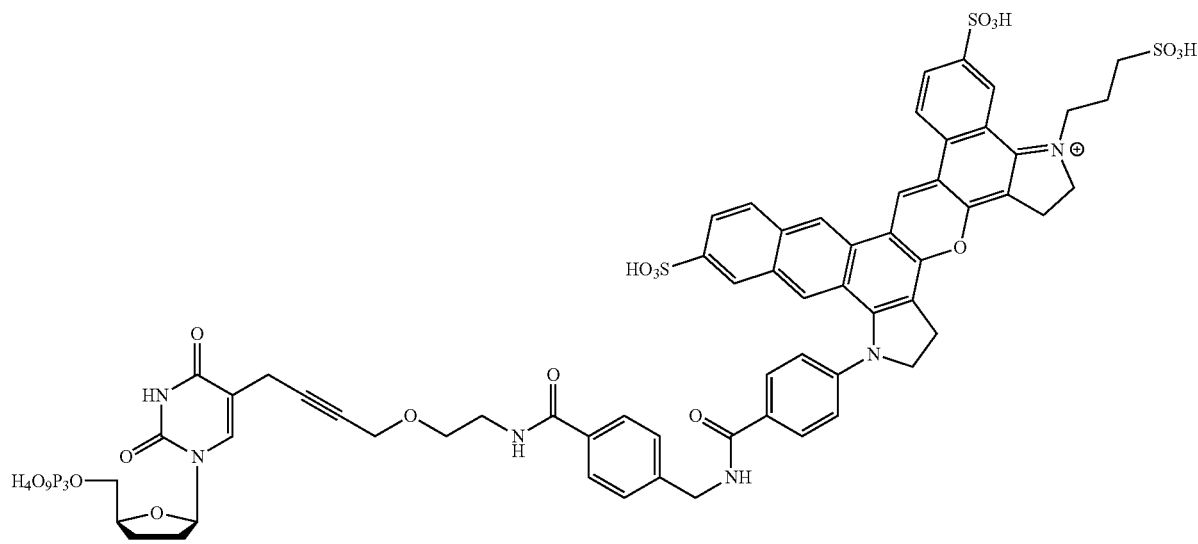

To a solution of 13 (9.2 μM, 10 μL) in NaHCO₃ (0.25 M, 50 μL) was added a solution of SNJ3 NHS ester (4-1) (1 mg/12 μL DMSO, 4 μL), followed by storing in the dark for 3 h. The mixture was purified on ion exchange HPLC and analytical reverse phase HPLC to give the corresponding product 30.

Synthesis of Compound (31)

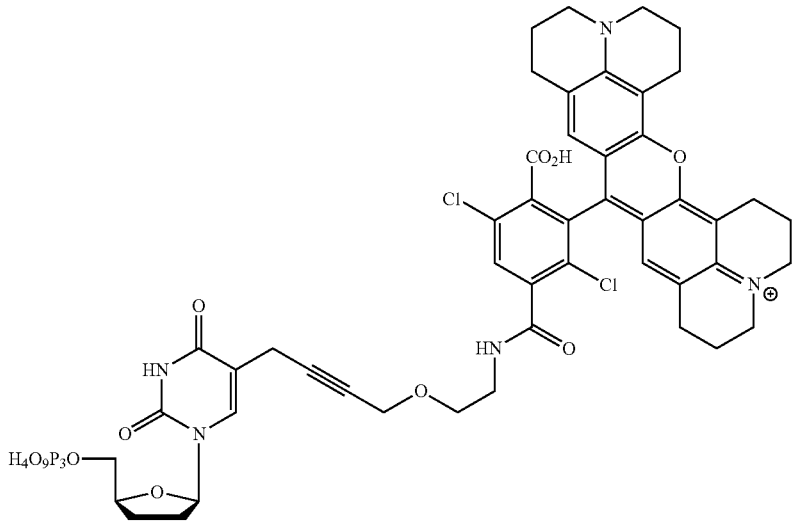

To a solution of 8 (17 mM, 10 μL) in NaHCO₃ (0.25 M, 50 μL) was added a solution of DRox-1 NHS ester (8 μL, 1 mg/12 μL DMSO), followed by storing in the dark for 2 h. The mixture was purified on ion exchange HPLC and analytical reverse phase HPLC to give the corresponding product 31 (32 μM, 100 μL).

Synthesis of Compound (32)
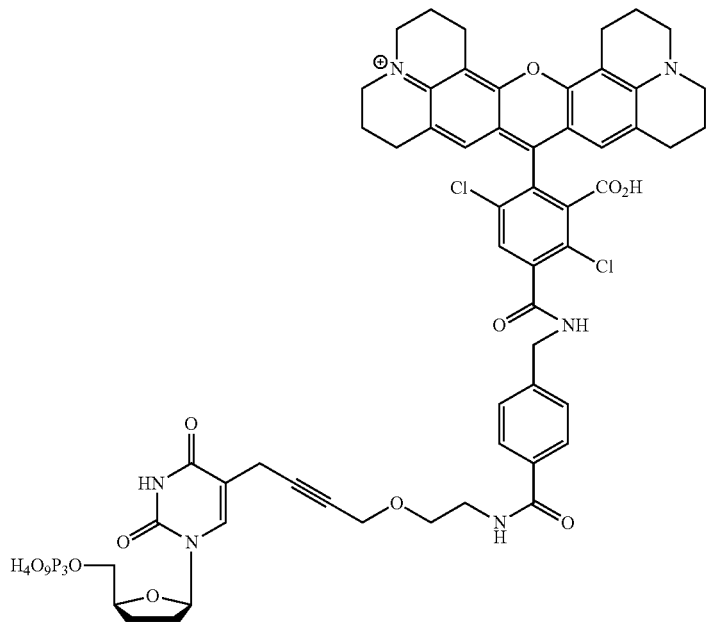
To a solution of 8 in NaHCO$_3$ (0.25 M, 50 μL) was added a solution of DRox-1 NHS ester (10 μL, 1 mg/12 μL DMSO), followed by storing in the dark for 2 h. The mixture was purified on ion exchange HPLC and reverse phase HPLC to give 32 (200 μM, 100 μL).
Synthesis of Compound (34)
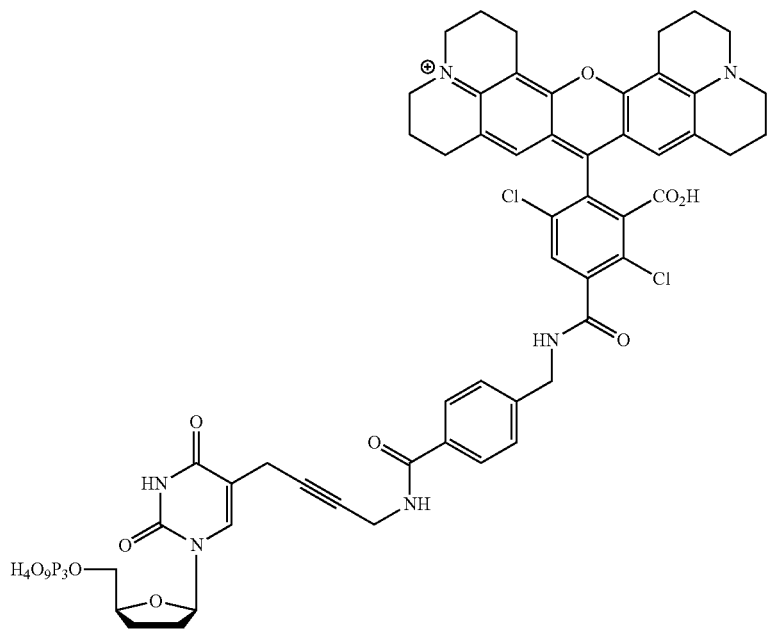

To a solution of 20 in NaHCO$_3$ (0.25 M, 100 μL) was added a solution of DRox-1 NHS ester (8 μL, 1 mg/12 μL DMSO), followed by storing in the dark for 4 h and then purification on ion exchange HPLC and reverse phase HPLC to give 34 (100 μM, 465 μL).

We claim:

1. A compound having a structure of Formula III:

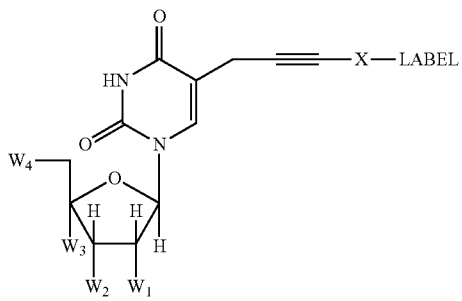

Formula III wherein

X is a bond or a linker,

LABEL is a detectable label, $W_1$ taken alone is H or OH, $W_2$ is OH or a non-extendable moiety, $W_3$ when taken alone is H or when taken together with $W_1$ is —CH$_2$—O—, and $W_4$ is selected from the group consisting of OH, monophosphoryl, diphosphoryl and triphosphoryl.

2. The compound of claim 1, wherein $W_1$ is H.

3. The compound of claim 1, wherein $W_2$ is selected from the group consisting of H, azido, amino, fluoro, chloro and methoxy.

4. The compound of claim 1, wherein $W_1$ is OH.

5. The compound of claim 1, wherein $W_2$ is OH.

6. The compound of claim 1, wherein $W_4$ is selected from the group consisting of monophosphoryl, diphosphoryl and triphosphoryl.

7. The compound of claim 1, wherein $W_4$ is triphosphoryl.

8. The compound of claim 1, wherein LABEL is selected from the group consisting of a fluorescent dye, an energy transfer dye, a quencher, and biotin.

9. The compound of claim 1, wherein LABEL is a fluorescent dye selected from the group consisting of a rhodamine dye, a fluorescein dye, a rhodol dye, a cyanine dye, a phthalocyanine dye and a squaraine dye.

10. The compound of claim 1, wherein the fluorescent dye is a fluorescein dye, a rhodamine dye or an energy transfer dye.

11. The compound of claim 1, wherein LABEL is an energy transfer dye which is a donor dye covalently attached to an acceptor dye, wherein either the donor dye or the acceptor dye is covalently attached to the linker, and the acceptor dye is capable of absorbing light emitted by the donor dye.

12. The compound of claim 11, wherein the donor dye is selected from the group consisting of a fluorescein dye and a rhodamine dye.

13. The compound of claim 11, wherein the acceptor dye is selected from the group consisting of a rhodamine dye, a fluorescein dye, a cyanine dye and a non-fluorescent quencher.

14. The compound of claim 1, wherein X is the linker and is selected from the group consisting of diradicals having a structure of one of the following formulae:

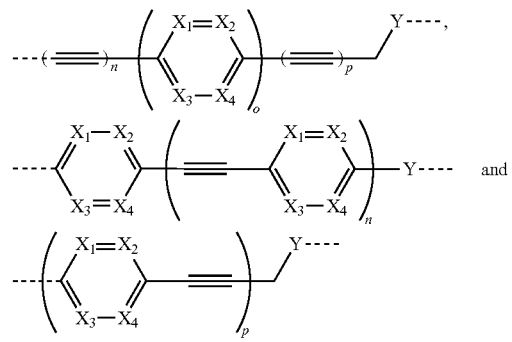

wherein n is an integer from 0 to 9;

o is an integer from 1 to 10;

p is an integer from 1 to 10;

each of $X_1$, $X_2$, $X_3$ and $X_4$ is independently a ring carbon substituted with hydrogen or a ring nitrogen;

Y is selected from the group consisting of oxygen, sulfur, unsubstituted amino, phosphonyl and phosphoryl, wherein Y is covalently attached to a further linker element or to the LABEL moiety; and the bond connection at the other end of the diradical is covalently attached to a further linker element or to the acetylenic carbon of the propargyl group attached to the nucleobase ring of the compound.

15. The compound of claim 14, wherein the further linker is a diradical selected from the group consisting of:

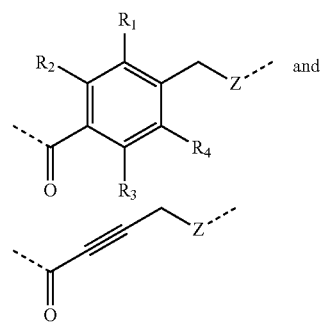

wherein each $R_1$, $R_2$, $R_3$ and $R_4$ is independently selected from the group consisting of H, halogen, F, Cl, Br, I, alkyl and $C_1$-$C_{10}$ aryl;

each Z is independently selected from the group consisting of oxygen, sulfur and NH; and the carbonyl carbon of the diradical linker is covalently attached to Y.

16. The compound of claim 1, wherein X is the linker and is selected from the group consisting of diradicals having a structure selected from the group consisting of:

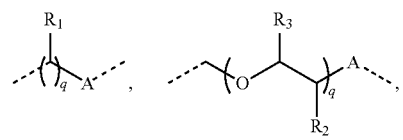

-continued

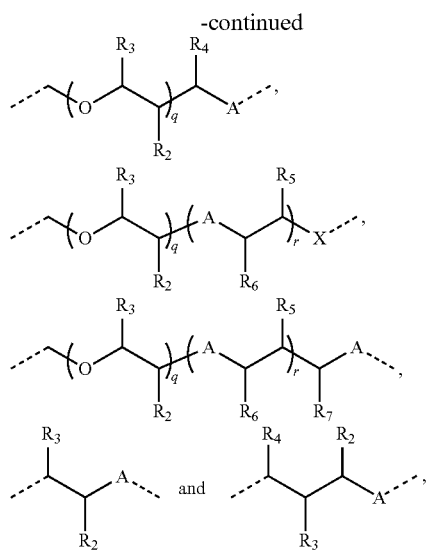

wherein
each A is independently selected from the group consisting of oxygen, sulfur, —NR— and —NH—;
each R, $R_1$, $R_2$, $R_3$, $R_4$, $R_5$, $R_6$ and $R_7$, taken alone, is independently selected from the group consisting of H, and C1-C4 alkyl; or when taken together:
$R_2$ together with one of $R_3$ or $R_4$ forms a carbocyclic ring having from 5-7 carbon atoms; or
$R_3$ together with one of $R_2$ or $R_4$ forms a substituted carbocyclic ring having from 5-7 carbon atoms; or
$R_5$ together with $R_6$ forms a carbocyclic ring having from 5-7 carbon atoms;
q is an integer from 1-10;
r is an integer from 1-10;
the A at the right hand terminus of the diradical linker is covalently attached to a further linker element or to the detectable label, and
the opposite end of the diradical is covalently attached to a further linker element or to the acetylenic carbon of the propargyl group attached to the nucleobase ring of the compound.

17. The compound of claim 16, wherein the further linker is a diradical selected from the group consisting of:

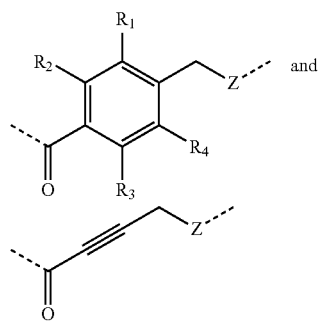

wherein each $R_1$, $R_2$, $R_3$ and $R_4$ is independently selected from the group consisting of H, halogen, F, Cl, Br, I, alkyl and $C_1$-$C_{10}$ aryl;
each Z is independently selected from the group consisting of oxygen, sulfur and NH; and
the carbonyl carbon of the diradical linker is covalently attached to X at the right hand terminus of the diradical linker of the formulae group of claim 16.

18. The compound of claim 1, wherein X is the linker and is selected from the group consisting of diradicals selected from the group consisting of:

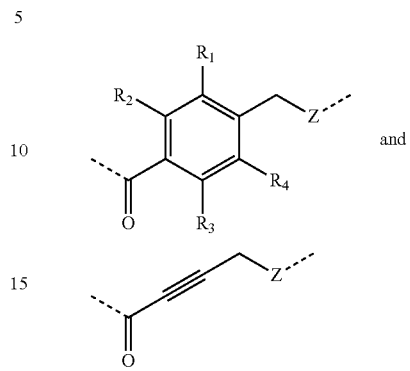

wherein each $R_1$, $R_2$, $R_3$ and $R_4$ is independently selected from the group consisting of H, halogen, F, Cl, Br, I, alkyl and $C_1$-$C_{10}$ aryl;
each Z is independently selected from the group consisting of oxygen, sulfur and an unsubstituted amino group; and
the carbonyl carbon of the diradical is covalently attached to the acetylenic carbon of the propargyl group attached to the nucleobase ring of the compound.

19. The compound of claim 1, wherein X is the linker and is selected from the group consisting of diradicals, having an amine terminus and an opposite terminus, selected from group consisting of:

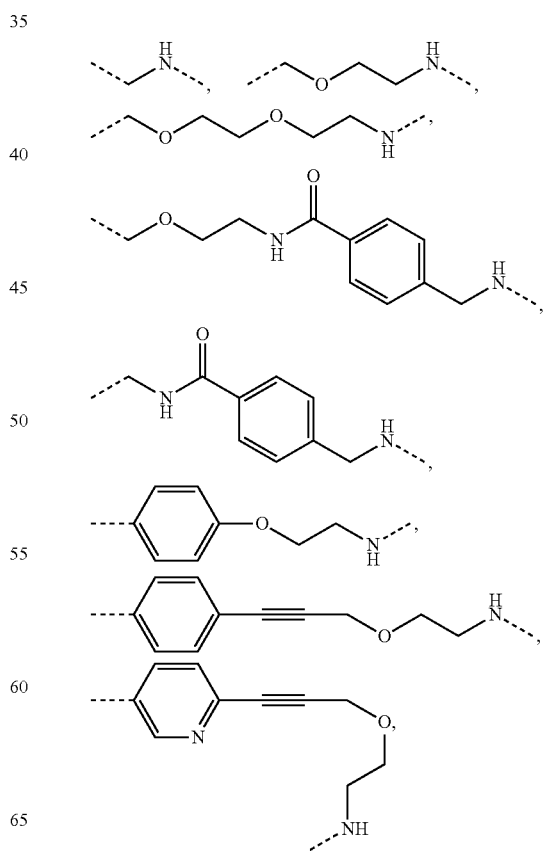

-continued

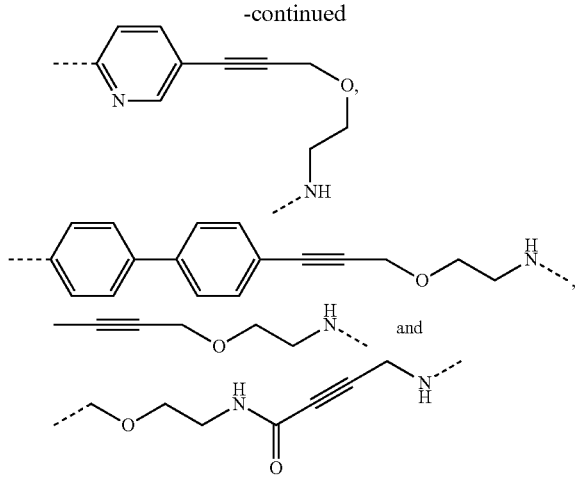

wherein the amine terminus is covalently attached to a label and the opposite terminus is covalently attached to the acetylene carbon atom of the propargyl group of the compound.

20. A compound having a structure of Formula III:

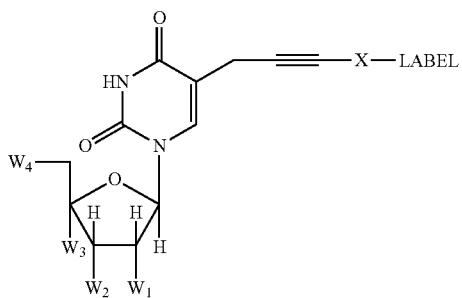

Formula III
wherein
LABEL is a detectable label;
$W_1$ taken alone is H or OH;
$W_2$ is OH or a non-extendable moiety;
$W_3$ when taken alone is H or when taken together with $W_1$ is —CH$_2$—O;
$W_4$ is selected from the group consisting of OH, monophosphoryl, diphosphoryl and triphosphoryl; and
X is a linker selected from the group consisting of:

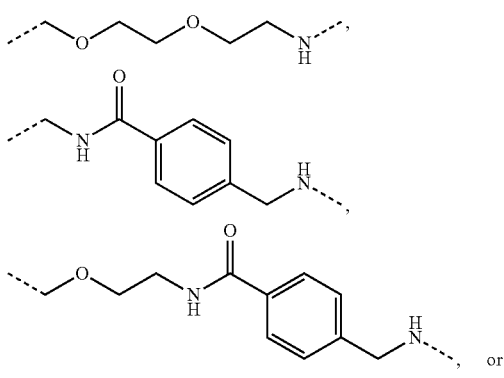

-continued

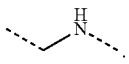

21. The compound of claim 20, wherein LABEL is selected from the group consisting of a fluorescent dye, an energy transfer dye, a quencher and biotin.

22. The compound of claim 20, wherein LABEL is an energy transfer dye which is a donor dye covalently attached to an acceptor dye, wherein either the donor dye or the acceptor dye is covalently attached to the linker, and the acceptor dye is capable of absorbing light emitted by the donor dye.

23. A compound having a structure of Formula III:

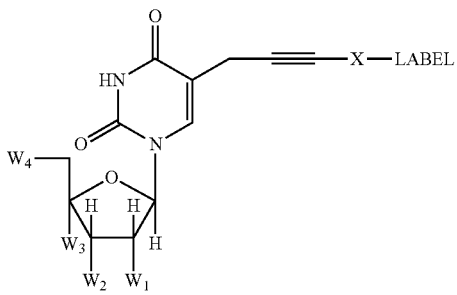

Formula III wherein
X is a bond or is 1 or 2 linkers;
LABEL is 1 or 2 detectable labels;
$W_1$ taken alone is H or OH;
$W_2$ is OH or a non-extendable moiety,
$W_3$ when taken alone is H or when taken together with $W_1$ is —CH$_2$—O; and
$W_4$ is selected from the group consisting of OH, monophosphoryl, diphosphoryl and triphosphoryl.

24. The compound of claim 23, wherein $W_1$ is H.

25. The compound of claim 23, wherein $W_2$ is selected from the group consisting of H, azido, amino, fluoro, chloro and methoxy.

26. The compound of claim 23, wherein $W_1$ is OH.

27. The compound of claim 23, wherein $W_2$ is OH.

28. The compound of claim 23, wherein $W_4$ is selected from the group consisting of monophosphoryl, diphosphoryl and triphosphoryl.

29. The compound of claim 23, wherein $W_4$ is triphosphoryl.

30. The compound of claim 23, wherein LABEL is selected from the group consisting of a fluorescent dye, an energy transfer dye, a quencher, and biotin.

31. The compound of claim 23, wherein LABEL is a fluorescent dye selected from a group consisting of a rhodamine dye, a fluorescein dye, a rhodol dye, a cyanine dye, a phthalocyanine dye and a squaraine dye.

32. The compound of claim 23, wherein the fluorescent dye is a fluorescein dye, a rhodamine dye or an energy transfer dye.

33. The compound of claim 23, wherein LABEL is an energy transfer dye consisting of a donor dye covalently attached to an acceptor dye, wherein either the donor dye or the acceptor dye is covalently attached to the linker, and the acceptor dye is capable of absorbing light emitted by the donor dye.

34. The compound of claim 23, wherein the donor dye is a fluorescein dye or a rhodamine dye.

35. The compound of claim 23, wherein the acceptor dye is a rhodamine dye, a fluorescein dye, a cyanine dye or a non-fluorescent quencher.

36. The compound of claim 23, wherein X is a linker, and the linker is a diradical having a structure of one of the following formulae:

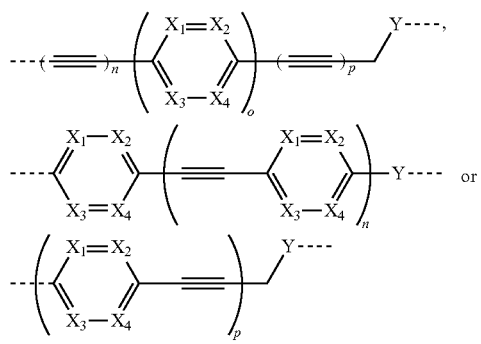

wherein
n is an integer from 0 to 9;
o is an integer from 1 to 10;
p is an integer from 1 to 10;
each of $X_1$, $X_2$, $X_3$ and $X_4$ is independently a ring carbon substituted with hydrogen or a ring nitrogen;
Y is selected from the group consisting of oxygen, sulfur, unsubstituted amino, phosphonyl and phosphoryl, wherein Y is covalently attached to a further linker element or to the LABEL moiety; and
the bond connection to the other end of the diradical is covalently attached a further linker element or to the acetylenic carbon of the propargyl group attached to the nucleobase ring of the compound.

37. The compound of claim 36, wherein the further linker is a diradical selected from the group consisting of:

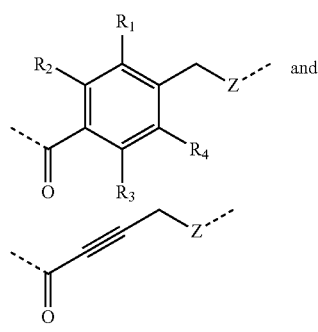

wherein each $R_1$, $R_2$, $R_3$ and $R_4$ is independently selected from the group consisting of H, halogen, F, Cl, Br, I, alkyl and $C_1$-$C_{10}$ aryl;
each Z is independently selected from the group consisting of oxygen, sulfur and NH; and
the carbonyl carbon of the diradical linker is covalently attached to Y.

38. The compound of claim 23, wherein X is a linker, and the linker is a diradical having a structure selected from the group consisting of:

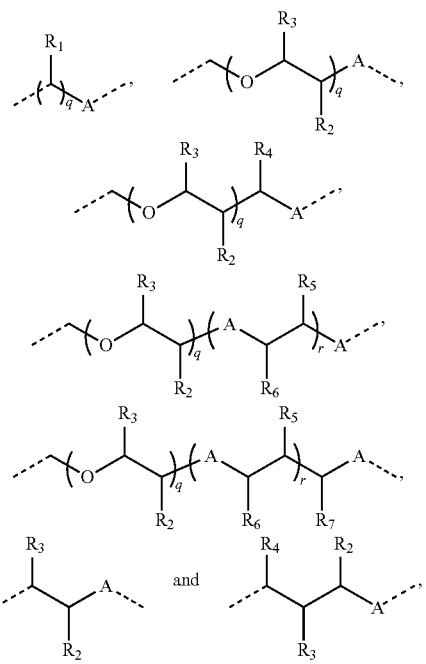

wherein
each A is independently selected from the group consisting of oxygen, sulfur, —NR— and —NH—;
each R, $R_1$, $R_2$, $R_3$, $R_4$, $R_5$, $R_6$ and $R_7$, taken alone, is independently selected from the group consisting of H, and C1-C4 alkyl; or when taken together:
$R_2$ together with one of $R_3$ or $R_4$ forms a carbocyclic ring having from 5-7 carbon atoms; or
$R_3$ together with one of $R_2$ or $R_4$ forms a substituted carbocyclic ring having from 5-7 carbon atoms; or
$R_5$ together with $R_6$ forms a carbocyclic ring having from 5-7 carbon atoms;
q is an integer from 1-10;
r is an integer from 1-10;
the A at the right hand terminus of the diradical linker is covalently attached to a further linker element or to the detectable label, and
the opposite end of the diradical is covalently attached to a further linker element or to the acetylenic carbon of the propargyl group attached to the nucleobase ring of the compound.

39. The compound of claim 23, wherein X is a linker and the linker is a diradical selected from the group consisting of:

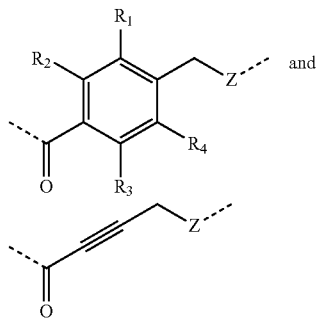

wherein each $R_1$, $R_2$, $R_3$ and $R_4$ is independently selected from the group consisting of H, halogen, F, Cl, Br, I, alkyl and $C_1$-$C_{10}$ aryl;

each Z is independently selected from the group consisting of oxygen, sulfur and an unsubstituted amino group; and the carbonyl carbon of the diradical is covalently attached to the acetylenic carbon of the propargyl group attached to the nucleobase ring of the compound.

40. The compound of claim 23, wherein X is a linker, and the linker is a diradical, having an amine terminus and an opposite terminus, selected from group consisting of:

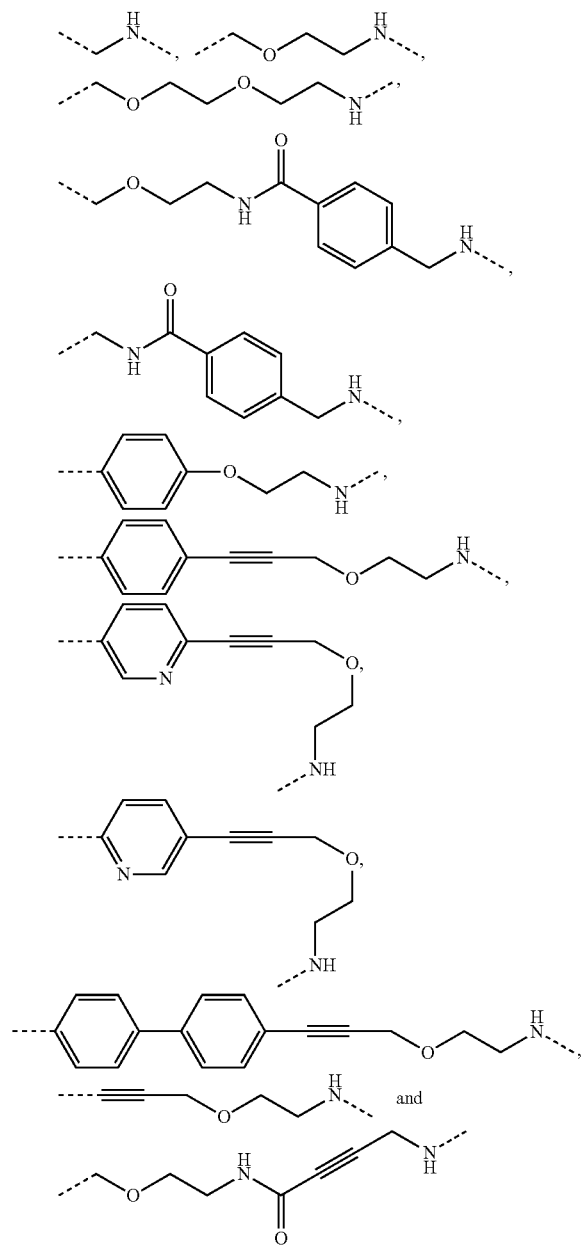

wherein the amine terminus is covalently attached to a label and the opposite terminus is covalently attached to the acetylene carbon atom of the propargyl group of the compound.

41. A compound having a structure of Formula III:

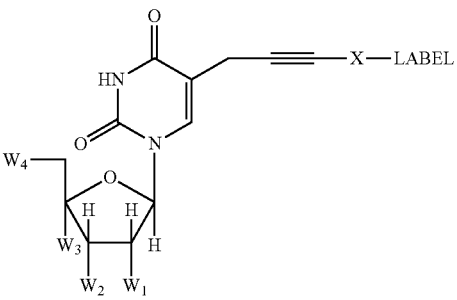

Formula III wherein

LABEL is 1 or 2 detectable labels;

$W_1$ taken alone is H or OH;

$W_2$ is OH or a non-extendable moiety;

$W_3$ when taken alone is H or when taken together with $W_1$ is —$CH_2$—O;

$W_4$ is selected from the group consisting of OH, monophosphoryl, diphosphoryl and triphosphoryl; and X is a linker selected from the group consisting of:

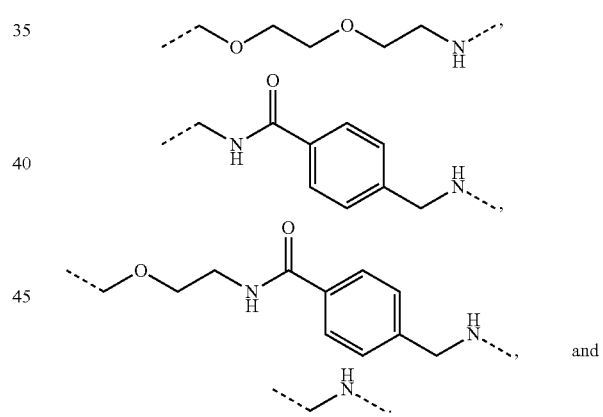

42. The compound of claim 41, wherein LABEL is selected from the group consisting of a fluorescent dye, an energy transfer dye, a quencher, and biotin.

43. The compound of claim 41, wherein LABEL is an energy transfer dye consisting of a donor dye covalently attached to an acceptor dye, wherein either the donor dye or the acceptor dye is covalently attached to the linker, and the acceptor dye is capable of absorbing light emitted by the donor dye.

* * * * *

UNITED STATES PATENT AND TRADEMARK OFFICE
CERTIFICATE OF CORRECTION

PATENT NO. : 8,835,625 B2
APPLICATION NO. : 13/470181
DATED : September 16, 2014
INVENTOR(S) : Barnett Rosenblum et al.

It is certified that error appears in the above-identified patent and that said Letters Patent is hereby corrected as shown below:

Title Page

- Related U.S. Application Data, reads
  "(63) Continuation of patent application No. 12/649,285, filed on May 11, 2012, now abandoned, which is a continuation of application No. 11/104,130, filed on Dec. 29, 2009,"
  should read -- (63) Continuation of patent application No. 12/649,285, filed on Dec. 29, 2009, now abandoned, which is a continuation of application No. 11/104,130, filed on Apr. 12, 2005, --

In the Claims

- Column 51, Claim 10, Line 50, reads "The compound of claim 1"
  should read -- The compound of claim 8 --

- Column 53, Claim 16, Line 10, reads

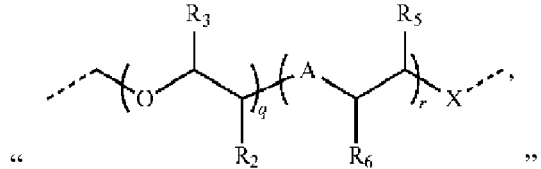

"  "

Signed and Sealed this
Twenty-second Day of March, 2016

Michelle K. Lee
*Director of the United States Patent and Trademark Office*

CERTIFICATE OF CORRECTION (continued)
U.S. Pat. No. 8,835,625 B2 should read

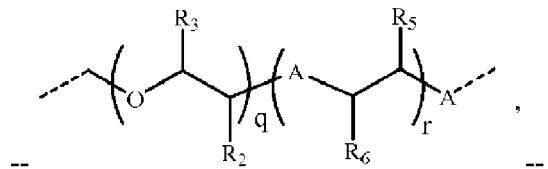

• Column 55, Claim 19, Line 13, reads

" 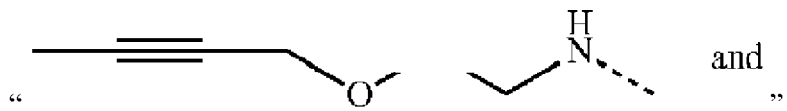 and "

should read

-- 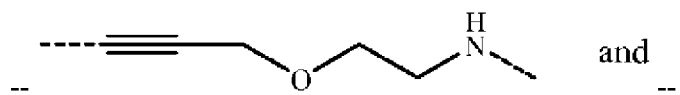 and --

• Column 55, Claim 20, Line 65, reads "or"

should read -- and --

• Column 56, Claim 32, Line 59, reads "The compound of claim 23"

should read -- The compound of claim 30 --

• Column 57, Claim 34, Line 1, reads "The compound of claim 23"

should read -- The compound of claim 33 --

• Column 57, Claim 35, Line 3, reads "The compound of claim 23"

should read -- The compound of claim 33 --